United States Patent
Morin et al.

(10) Patent No.: US 10,548,722 B2
(45) Date of Patent: Feb. 4, 2020

(54) PROSTHETIC HEART VALVE WITH PARAVALVULAR LEAK MITIGATION FEATURES

(71) Applicant: St. Jude Medical, Cardiology Division, Inc., St. Paul, MN (US)

(72) Inventors: Kristen T. Morin, Saint Paul, MN (US); Gary Erzberger, Plymouth, MN (US); Brett A. Hillukka, Hanover, MN (US); Kristopher H. Vietmeier, Monticello, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 64 days.

(21) Appl. No.: 15/686,310

(22) Filed: Aug. 25, 2017

(65) Prior Publication Data

US 2018/0055631 A1    Mar. 1, 2018

Related U.S. Application Data

(60) Provisional application No. 62/505,371, filed on May 12, 2017, provisional application No. 62/379,869, filed on Aug. 26, 2016.

(51) Int. Cl.
*A61F 2/82* (2013.01)
*A61F 2/24* (2006.01)
*A61F 2/07* (2013.01)

(52) U.S. Cl.
CPC .............. *A61F 2/2412* (2013.01); *A61F 2/07* (2013.01); *A61F 2/2409* (2013.01);
(Continued)

(58) Field of Classification Search
CPC ..................................... A61F 2/82; A61F 2/24
See application file for complete search history.

(56) References Cited

U.S. PATENT DOCUMENTS

| 3,657,744 A | 4/1972 | Ersek |
| 4,275,469 A | 6/1981 | Gabbay |
(Continued)

FOREIGN PATENT DOCUMENTS

| DE | 19857887 B4 | 5/2005 |
| DE | 10121210 B4 | 11/2005 |
(Continued)

OTHER PUBLICATIONS

Andersen, H. R., et al., "Transluminal implantation of artificial heart valves", European Heart Journal, (1992), vol. 13, Issue 5, 704-708.
(Continued)

*Primary Examiner* — Matthew W Schall
(74) *Attorney, Agent, or Firm* — Lerner, David, Littenberg, Krumholz & Mentlik, LLP

(57) ABSTRACT

A prosthetic heart valve includes a collapsible stent and a valve assembly disposed within the stent. A first cuff is disposed adjacent the stent. A second cuff having a distal edge facing the outflow end of the stent is disposed about the stent radially outward of the first cuff and the stent. The stent may include a plurality of fingers each having a first end coupled to a corresponding cell of the stent and a free end adapted to extend radially outward of the corresponding cell. The distal edge of the second cuff may be coupled to the fingers at spaced locations around the circumference of the stent to position the distal edge radially outward from the corresponding cells at the spaced locations. Various stent struts may be tapered to reduce the stent circumference in the collapsed condition, and to improve the fatigue resistance and/or bendability of the stent.

21 Claims, 25 Drawing Sheets

(52) U.S. Cl.
CPC ................ *A61F 2210/0061* (2013.01); *A61F 2220/0025* (2013.01); *A61F 2250/0069* (2013.01)

(56) References Cited

U.S. PATENT DOCUMENTS

| | | | |
|---|---|---|---|
| 4,491,986 A | 1/1985 | Gabbay | |
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,415,664 A | 5/1995 | Pinchuk | |
| 5,480,423 A | 1/1996 | Ravenscroft et al. | |
| 5,843,167 A | 12/1998 | Dwyer et al. | |
| 5,855,601 A | 1/1999 | Bessler et al. | |
| 5,935,163 A | 8/1999 | Gabbay | |
| 5,961,549 A | 10/1999 | Nguyen et al. | |
| 6,045,576 A | 4/2000 | Starr et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,458,153 B1 | 10/2002 | Bailey et al. | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,652,578 B2 | 11/2003 | Bailey et al. | |
| 6,685,625 B2 | 2/2004 | Gabbay | |
| 6,716,244 B2 | 4/2004 | Klaco | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 6,951,573 B1 | 10/2005 | Dilling | |
| 7,018,406 B2 | 3/2006 | Seguin et al. | |
| 7,025,780 B2 | 4/2006 | Gabbay | |
| 7,137,184 B2 | 11/2006 | Schreck | |
| 7,147,661 B2 | 12/2006 | Chobotov et al. | |
| 7,160,322 B2 | 1/2007 | Gabbay | |
| 7,195,641 B2 | 3/2007 | Palmaz et al. | |
| 7,247,167 B2 | 7/2007 | Gabbay | |
| 7,267,686 B2 | 9/2007 | DiMatteo et al. | |
| 7,276,078 B2 | 10/2007 | Spenser et al. | |
| 7,311,730 B2 | 12/2007 | Gabbay | |
| 7,320,704 B2 | 1/2008 | Lashinski et al. | |
| 7,329,278 B2 | 2/2008 | Seguin et al. | |
| 7,374,573 B2 | 5/2008 | Gabbay | |
| 7,381,218 B2 | 6/2008 | Schreck | |
| 7,381,219 B2 | 6/2008 | Salahieh et al. | |
| 7,452,371 B2 | 11/2008 | Pavcnik et al. | |
| 7,510,572 B2 | 3/2009 | Gabbay | |
| 7,510,575 B2 | 3/2009 | Spenser et al. | |
| 7,524,331 B2 | 4/2009 | Birdsall | |
| 7,534,261 B2 | 5/2009 | Friedman | |
| RE40,816 E | 6/2009 | Taylor et al. | |
| 7,585,321 B2 | 9/2009 | Cribier | |
| 7,628,805 B2 | 12/2009 | Spenser et al. | |
| 7,682,390 B2 | 3/2010 | Seguin | |
| 7,708,775 B2 | 5/2010 | Rowe et al. | |
| 7,731,742 B2 | 6/2010 | Schlick et al. | |
| 7,748,389 B2 | 7/2010 | Salahieh et al. | |
| 7,780,725 B2 | 8/2010 | Haug et al. | |
| 7,799,069 B2 | 9/2010 | Bailey et al. | |
| 7,803,185 B2 | 9/2010 | Gabbay | |
| 7,824,442 B2 | 11/2010 | Salahieh et al. | |
| 7,837,727 B2 | 11/2010 | Goetz et al. | |
| 7,846,203 B2 | 12/2010 | Cribier | |
| 7,846,204 B2 | 12/2010 | Letac et al. | |
| 7,892,281 B2 | 2/2011 | Seguin et al. | |
| 7,914,569 B2 | 3/2011 | Nguyen et al. | |
| 7,959,666 B2 | 6/2011 | Salahieh et al. | |
| 7,959,672 B2 | 6/2011 | Salahieh et al. | |
| 7,972,378 B2 | 7/2011 | Tabor et al. | |
| 7,988,724 B2 | 8/2011 | Salahieh et al. | |
| 7,993,394 B2 | 8/2011 | Hariton et al. | |
| 8,016,877 B2 | 9/2011 | Seguin et al. | |
| D648,854 S | 11/2011 | Braido | |
| 8,048,153 B2 | 11/2011 | Salahieh et al. | |
| 8,052,741 B2 | 11/2011 | Bruszewski et al. | |
| 8,052,749 B2 | 11/2011 | Salahieh et al. | |
| 8,052,750 B2 | 11/2011 | Tuval et al. | |
| 8,062,355 B2 | 11/2011 | Figulla et al. | |
| 8,075,611 B2 | 12/2011 | Millwee et al. | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| 8,137,398 B2 | 3/2012 | Tuval et al. | |
| 8,142,497 B2 | 3/2012 | Friedman | |
| D660,432 S | 5/2012 | Braido | |
| D660,433 S | 5/2012 | Braido et al. | |
| D660,967 S | 5/2012 | Braido et al. | |
| 8,182,528 B2 | 5/2012 | Salahieh et al. | |
| 8,221,493 B2 | 7/2012 | Boyle et al. | |
| 8,230,717 B2 | 7/2012 | Matonick | |
| 8,231,670 B2 | 7/2012 | Salahieh et al. | |
| 8,252,051 B2 | 8/2012 | Chau et al. | |
| 8,308,798 B2 | 11/2012 | Pintor et al. | |
| 8,313,525 B2 | 11/2012 | Tuval et al. | |
| 8,323,335 B2 | 12/2012 | Rowe et al. | |
| 8,323,336 B2 | 12/2012 | Hill et al. | |
| 8,343,213 B2 | 1/2013 | Salahieh et al. | |
| 8,348,995 B2 | 1/2013 | Tuval et al. | |
| 8,348,996 B2 | 1/2013 | Tuval et al. | |
| 8,348,998 B2 | 1/2013 | Pintor et al. | |
| 8,366,769 B2 | 2/2013 | Huynh et al. | |
| 8,403,983 B2 | 3/2013 | Quadri et al. | |
| 8,408,214 B2 | 4/2013 | Spenser | |
| 8,414,643 B2 | 4/2013 | Tuval et al. | |
| 8,425,593 B2 | 4/2013 | Braido et al. | |
| 8,449,599 B2 | 5/2013 | Chau et al. | |
| 8,449,604 B2 | 5/2013 | Moaddeb et al. | |
| 8,454,686 B2 | 6/2013 | Alkhatib | |
| 8,500,798 B2 | 8/2013 | Rowe et al. | |
| 8,568,474 B2 | 10/2013 | Yeung et al. | |
| 8,579,962 B2 | 11/2013 | Salahieh et al. | |
| 8,579,966 B2 | 11/2013 | Seguin et al. | |
| 8,585,755 B2 | 11/2013 | Chau et al. | |
| 8,591,575 B2 | 11/2013 | Cribier | |
| 8,597,349 B2 | 12/2013 | Alkhatib | |
| 8,603,159 B2 | 12/2013 | Seguin et al. | |
| 8,603,160 B2 | 12/2013 | Salahieh et al. | |
| 8,613,765 B2 | 12/2013 | Bonhoeffer et al. | |
| 8,623,074 B2 | 1/2014 | Ryan | |
| 8,652,204 B2 | 2/2014 | Quill et al. | |
| 8,663,322 B2 | 3/2014 | Keranen | |
| 8,668,733 B2 | 3/2014 | Haug et al. | |
| 8,685,080 B2 | 4/2014 | White | |
| 8,728,154 B2 | 5/2014 | Alkhatib | |
| 8,747,459 B2 | 6/2014 | Nguyen et al. | |
| 8,764,820 B2 | 7/2014 | Dehdashtian et al. | |
| 8,784,481 B2 | 7/2014 | Alkhatib et al. | |
| 8,795,357 B2 | 8/2014 | Yohanan et al. | |
| 8,801,776 B2 | 8/2014 | House et al. | |
| 8,808,356 B2 | 8/2014 | Braido et al. | |
| 8,828,078 B2 | 9/2014 | Salahieh et al. | |
| 8,834,563 B2 | 9/2014 | Righini | |

(56) References Cited

U.S. PATENT DOCUMENTS

| | | |
|---|---|---|
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |
| 8,986,375 B2 | 3/2015 | Garde et al. |
| D730,520 S | 5/2015 | Braido et al. |
| D730,521 S | 5/2015 | Braido et al. |
| D732,666 S | 6/2015 | Nguyen et al. |
| D755,384 S | 5/2016 | Pesce et al. |
| D802,764 S | 11/2017 | Erzberger et al. |
| D802,765 S | 11/2017 | Erzberger et al. |
| D802,766 S | 11/2017 | Erzberger et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2003/0236567 A1 | 12/2003 | Elliot |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0210304 A1 | 10/2004 | Seguin et al. |
| 2004/0260389 A1 | 12/2004 | Case et al. |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0099653 A1 | 4/2009 | Sun et al. |
| 2009/0112309 A1 | 4/2009 | Jaramillo et al. |
| 2009/0138079 A1 | 5/2009 | Tuval et al. |
| 2009/0234443 A1 | 9/2009 | Ottma et al. |
| 2009/0276027 A1 | 11/2009 | Glynn |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0256737 A1 | 10/2010 | Pollock et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0264196 A1 | 10/2011 | Savage et al. |
| 2011/0264206 A1 | 10/2011 | Tabor |
| 2012/0035722 A1 | 2/2012 | Tuval |
| 2012/0078347 A1 | 3/2012 | Braido et al. |
| 2012/0101572 A1 | 4/2012 | Kovalsky et al. |
| 2012/0123529 A1 | 5/2012 | Levi et al. |
| 2012/0197390 A1* | 8/2012 | Alkhatib ............... A61F 2/2418 623/2.18 |
| 2012/0303116 A1 | 11/2012 | Gorman, II et al. |
| 2013/0274873 A1 | 10/2013 | Delaloye et al. |
| 2014/0121763 A1 | 5/2014 | Duffy et al. |
| 2014/0155997 A1 | 6/2014 | Braido |
| 2014/0194981 A1 | 7/2014 | Menk et al. |
| 2014/0214159 A1 | 7/2014 | Vidlund et al. |
| 2014/0228946 A1 | 8/2014 | Chau et al. |
| 2014/0277417 A1 | 9/2014 | Schraut et al. |
| 2014/0303719 A1 | 10/2014 | Cox et al. |
| 2014/0324164 A1 | 10/2014 | Gross et al. |
| 2014/0343670 A1 | 11/2014 | Bakis et al. |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |
| 2015/0018944 A1 | 1/2015 | O'Connell et al. |
| 2015/0142104 A1 | 5/2015 | Braido |
| 2015/0148893 A1 | 5/2015 | Braido et al. |
| 2015/0320556 A1 | 11/2015 | Levi et al. |
| 2015/0335429 A1 | 11/2015 | Morriss et al. |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 1926455 A2 | 6/2008 |
| EP | 2537487 A1 | 12/2012 |
| FR | 2847800 B1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 2001028459 A1 | 4/2001 |

(56) References Cited

FOREIGN PATENT DOCUMENTS

| WO | 2001049213 A2 | 7/2001 |
|---|---|---|
| WO | 0154625 A1 | 8/2001 |
| WO | 2001056500 A2 | 8/2001 |
| WO | 200176510 A2 | 10/2001 |
| WO | 0236048 A1 | 5/2002 |
| WO | 0247575 A2 | 6/2002 |
| WO | 2002067782 A2 | 9/2002 |
| WO | 2003047468 A1 | 6/2003 |
| WO | 2005070343 A1 | 8/2005 |
| WO | 06073626 A2 | 7/2006 |
| WO | 2007053243 A2 | 5/2007 |
| WO | 2007071436 A2 | 6/2007 |
| WO | 08070797 A2 | 6/2008 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2015126711 A1 | 8/2015 |
| WO | 2015152980 A1 | 10/2015 |

OTHER PUBLICATIONS

Andersen, Henning Rud, "Transluminal Catheter Implanted Prosthetic Heart Valves", International Journal of Angiology 7:102-106, 1998.
Buellesfeld et al., "Treatment of paravalvular leaks through inverventional techniques", Department of Cardiology, Ben University Hospital 2011.
Christoph H. Huber, et al., "Direct-Access Valve Replacement", Journal of the American College of Cardiology, vol. 46, No. 2, (Jul. 19, 2005).
De Cicco, Giuseppe, et al., "Aortic valve periprosthetic leakage: anatomic observations and surgical results", The Annals of thoracic surgery 79.5 (2005): 1480-1485.
Dewey et al., "Transapical aortic valve implantation: an animal feasibility study"; The annals of thoracic surgery 2006; 82: 110-6 (Feb. 13, 2006).
Gössl et al., "Percutaneous treatment of aortic and mitral valve paravalvular regurgitation", Current cardiology reports 15.8, 2013: 1-8.
Heat Advisor, "Heart repairs without surgery. Minimally invasive procedures aim to correct valve leakage", Sep. 2004, PubMed ID 15586429.
Hourihan et al., "Transcatheter Umbrella Closure of Valvular and Paravalvular Leaks", Journal of the American College of Cardiology, vol. 20, No. 6, pp. 1371-1377, (1992).
John G. Webb et al., "Percutaneous Aortic Valve Implantation Retrograde From the Femoral Artery", Circulation, 2006; 113:842-850 (Feb. 6, 2006).
Knudsen, L.L., et al., "Catheter-implanted prosthetic heart valves", The International Journal of Artificial Organs, vol. 16, No. 5 1993, pp. 253-262.
M. J. Mack, "Minimally invasive cardiac surgery", Surgical Endoscopy, 2006, 20:S488-S492, DOI: 10.1007/s00464-006-0110-8 (presented Apr. 24, 2006).
Moazami, Nader, et al., "Transluminal Aortic Valve Placement", ASAIO Journal, (1996); 42:M381-M385.
Muñoz et al., "Guidance of treatment of perivalvular prosthetic leaks", Current cardiology reports 16.1, Jan. 2014: 1-6.
Quaden, Rene et al., "Percutaneous aortic valve replacement: resection before implantation", 836-840, European J. of cardio-thoracic Surgery, 27 (2005).
Rohde et al., "Resection of Calcified Aortic Heart Leaflets In Vitro by Q-Switched 2μm Microsecond Laser Radiation", Journal of Cardiac Surgery, 30: 157-162, 2015, doi: 10.1111/jocs.12481.
Ruiz, Carlos, "Overview of PRE-CE Mark Transcatheter Aortic Valve Technologies", Euro PCR, dated May 25, 2010.
Samuel V. Lichtenstein et al., "Transapical Transcatheter Aortic Valve Implantation in Humans", Circulation. 2006; 114: 591-596 (Jul. 31, 2006).
Samuel V. Lichtenstein, "Closed heart surgery: Back to the future", The Journal of Thoracic and Cardiovascular Surgery, 2006, vol. 131, No. 5, pp. 941-943.
Swiatkiewicz, Iwona, et al., "Percutaneous closure of mitral perivalvular leak", Kardiologia polska 67.7 (2009): 762.
Textbook "Transcatheter Valve Repair", 2006, pp. 165-186.
Walther et al., "Transapical approach for sutureless stent-fixed aortic valve implantation: experimental results", European Journal of Cardio-thoracic Surgery 29 (2006) 703-708 (Jan. 30, 2006).
Zegdi, Rachid, MD, PhD et al., "Is It Reasonable to Treat All Calcified Stenotic Aortic Valves With a Valved Stent?", 579-584, J. of the American College of Cardiology, vol. 51, No. 5, Feb. 5, 2008.
International Search Report for Application No. PCT/US2017/048580 dated Nov. 16, 2017.

* cited by examiner

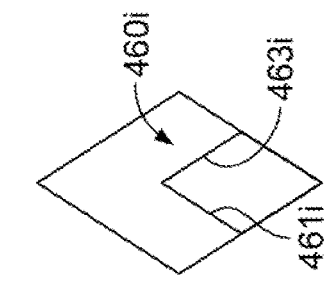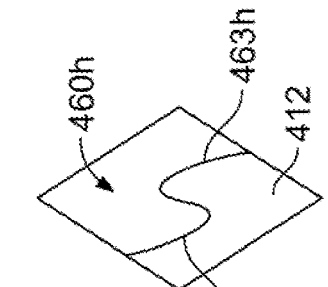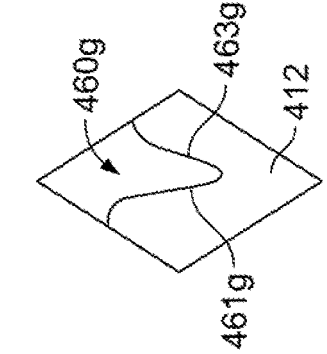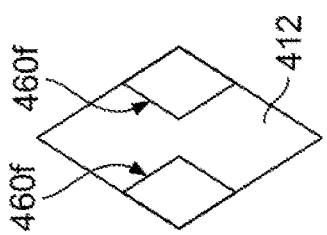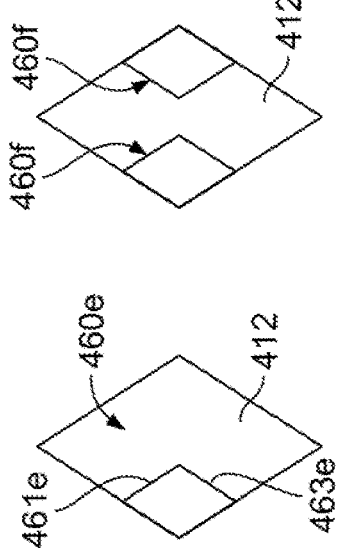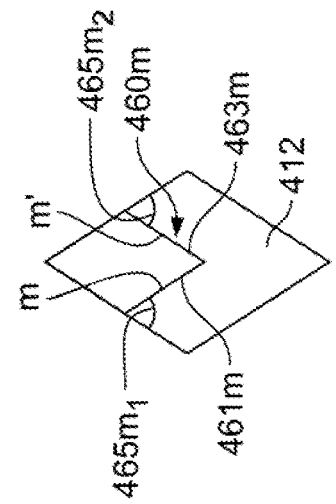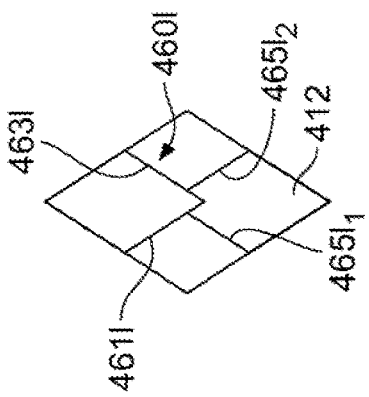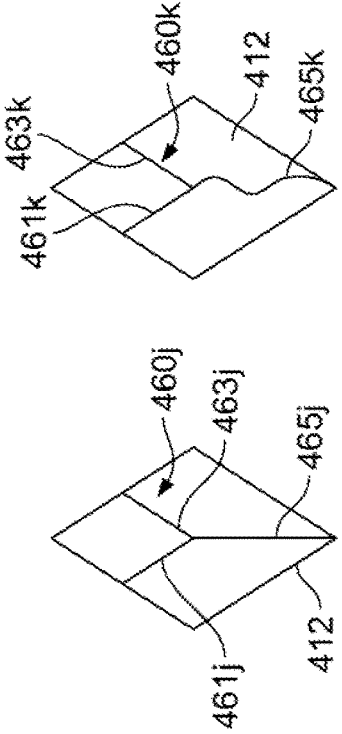

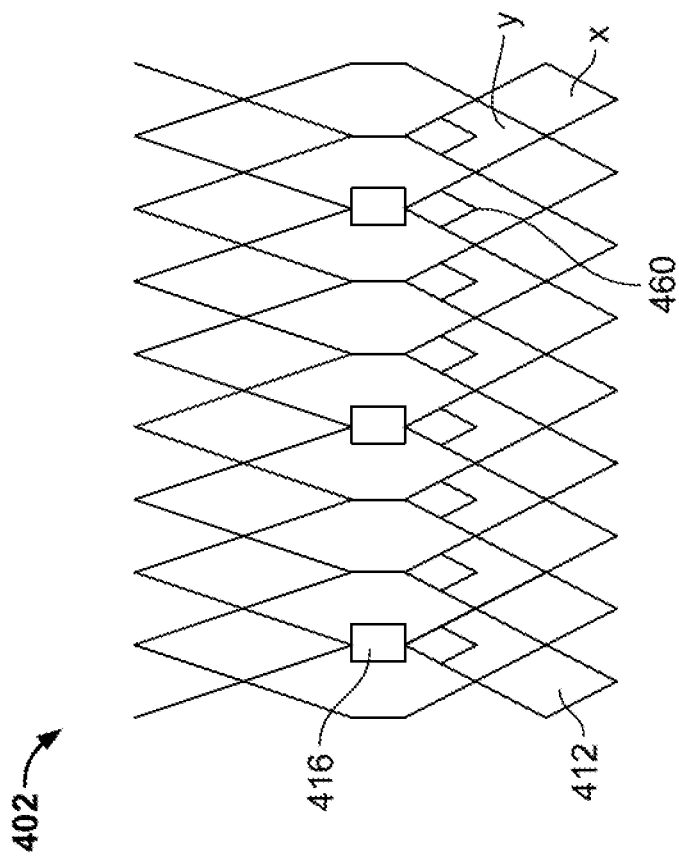
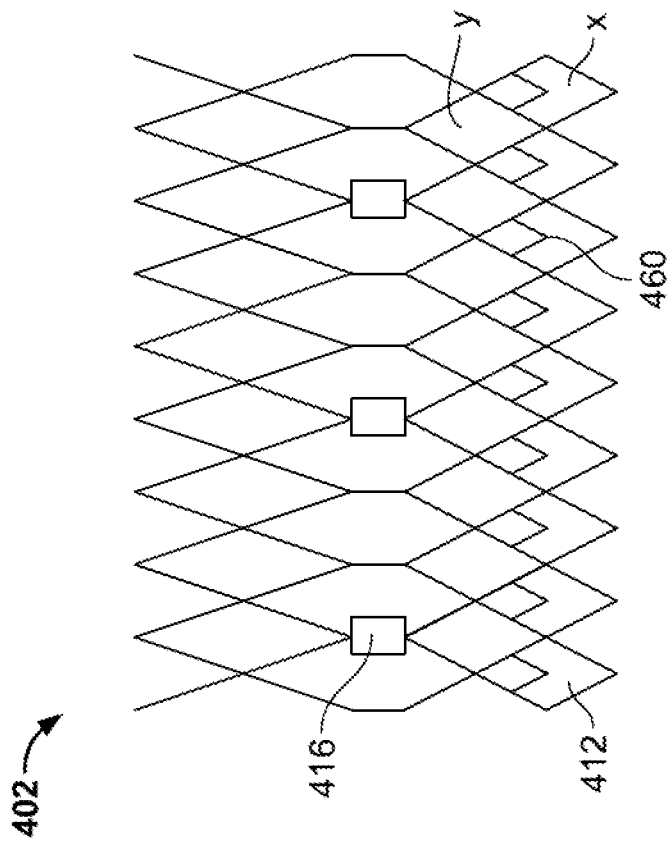

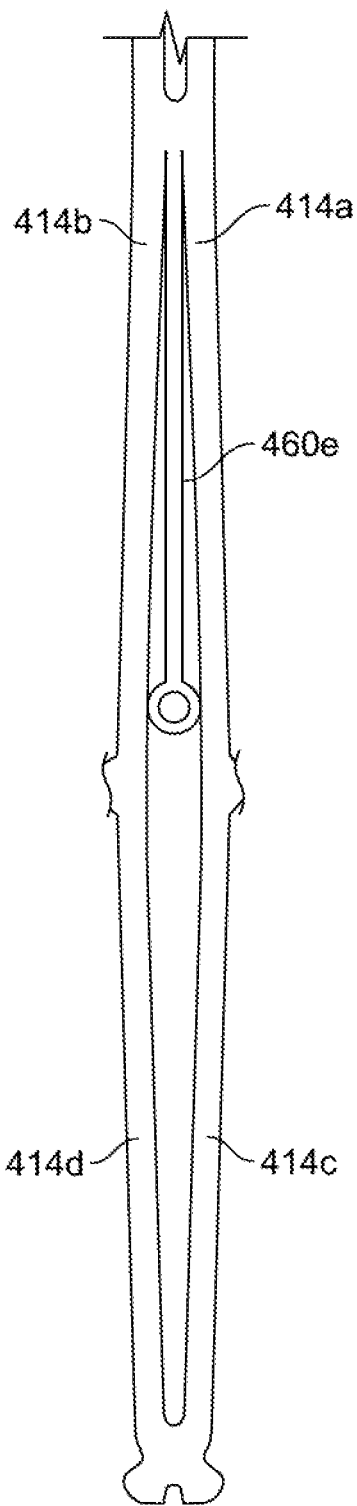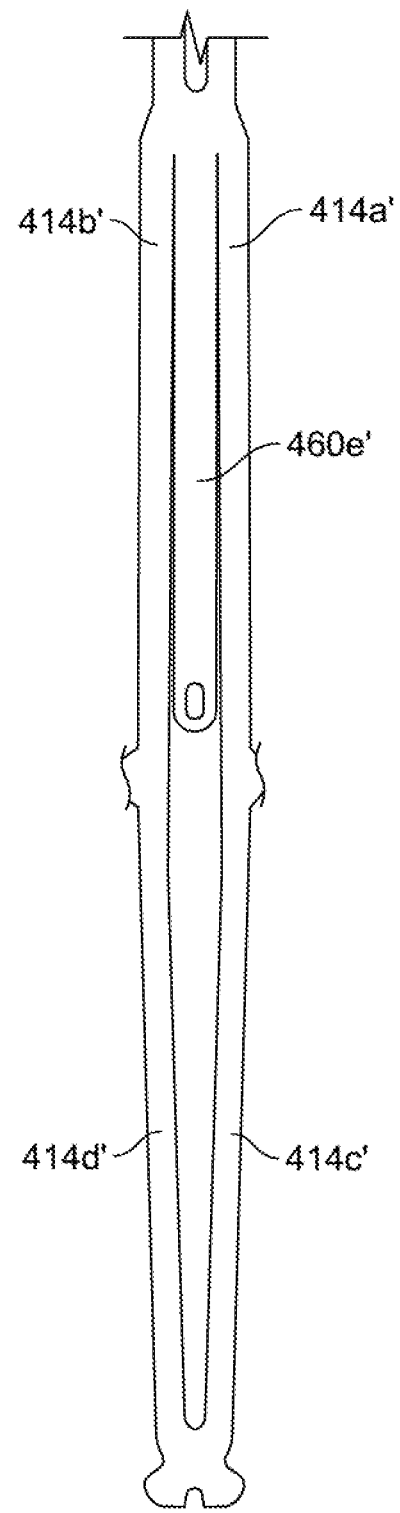
FIG. 7A  FIG. 7B

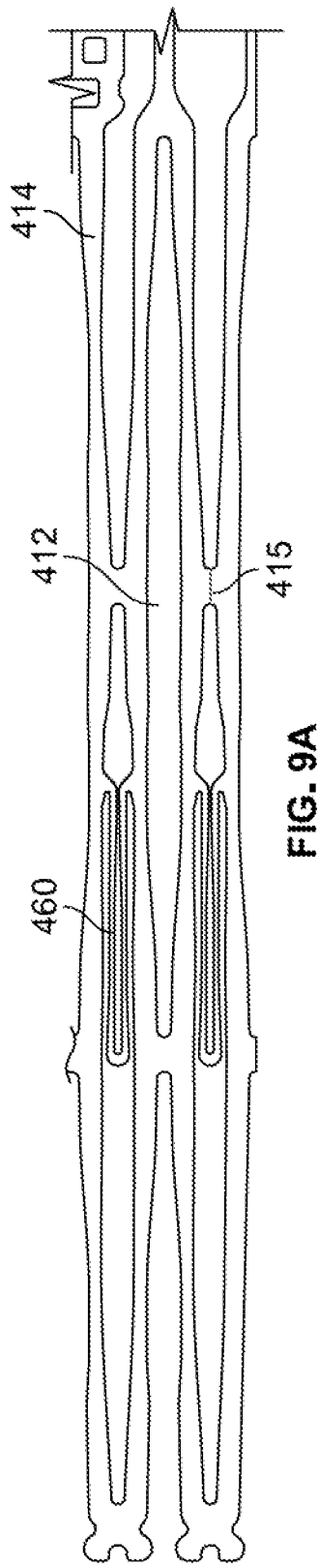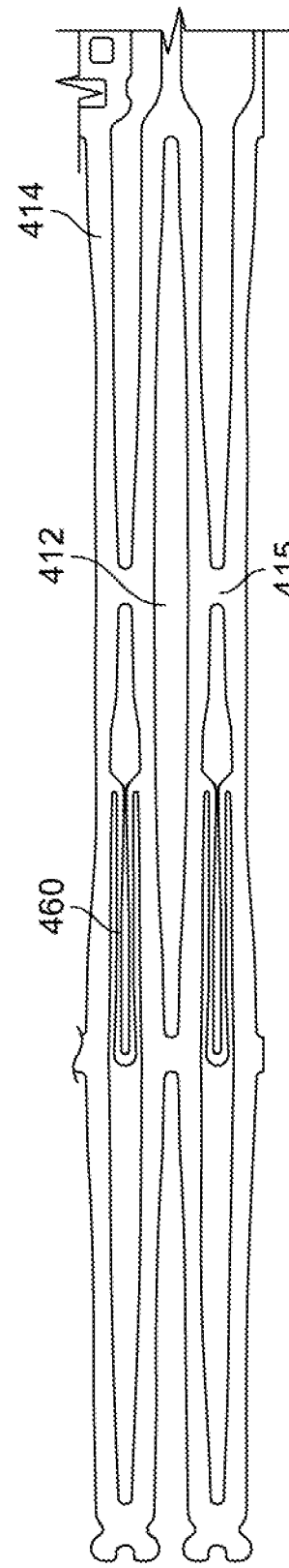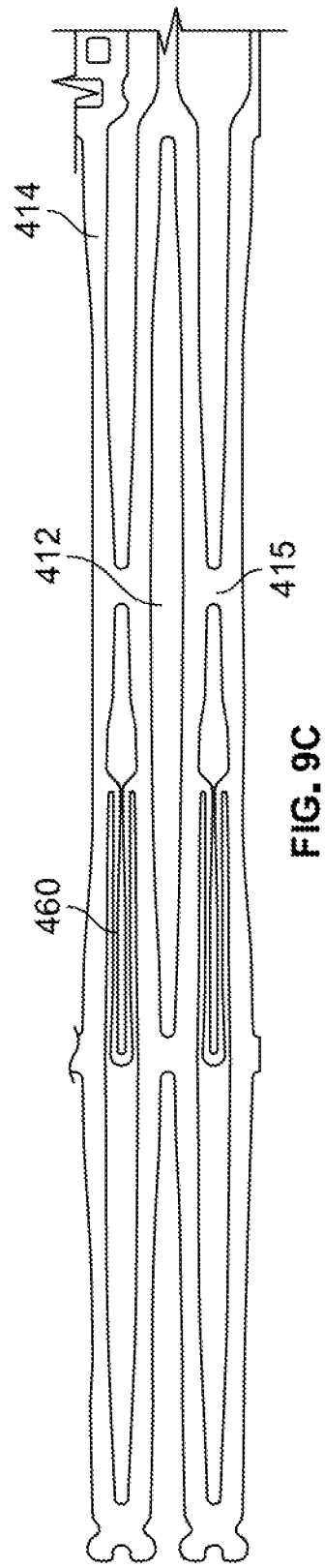

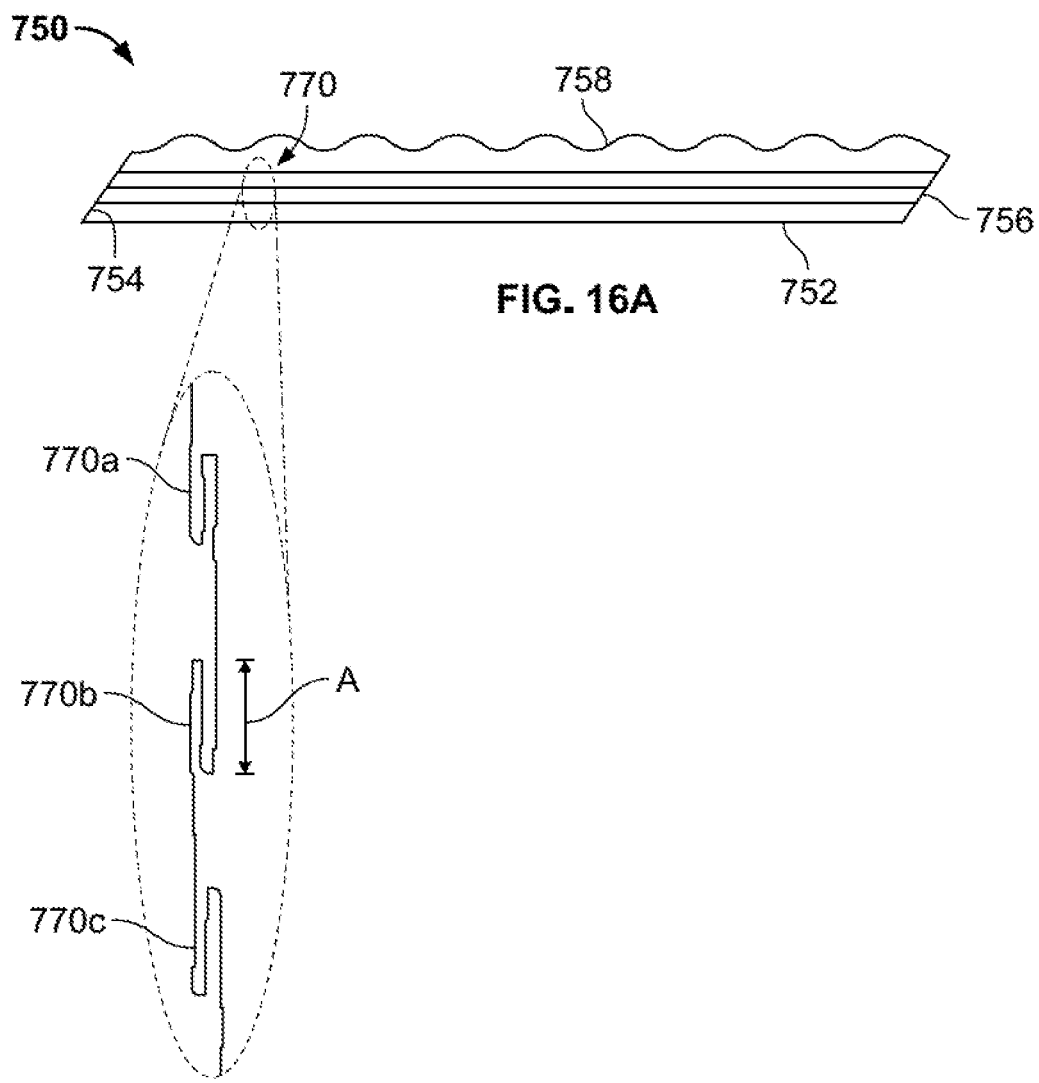
FIG. 16A
FIG. 16B
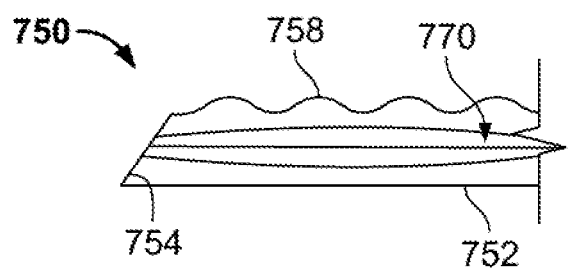
FIG. 16C

PROSTHETIC HEART VALVE WITH PARAVALVULAR LEAK MITIGATION FEATURES

CROSS-REFERENCE TO RELATED APPLICATIONS

This application claims the benefit of the filing dates of U.S. Provisional Patent Application No. 62/379,869 filed Aug. 26, 2016 and U.S. Provisional Patent Application No. 62/505,371 filed May 12, 2017, the disclosures of which are both hereby incorporated by reference herein.

BACKGROUND OF THE DISCLOSURE

The present disclosure relates to heart valve replacement and, in particular, to collapsible prosthetic heart valves. More particularly, the present disclosure relates to collapsible prosthetic transcatheter heart valves that are easier to load into a delivery device and that minimize or reduce paravalvular leaks.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent and a balloon-expandable stent. To load such valves into a delivery apparatus and deliver them into a patient, the valve is first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as a sheath covering the valve is withdrawn.

After implantation, imperfect sealing between the prosthetic valve and the native tissue at the site of implantation may cause complications such as paravalvular leakage ("PV leak") in which retrograde blood flows through one or more gaps formed between the structure of the implanted valve and cardiac tissue as a result of the imperfect sealing.

BRIEF SUMMARY

According to one embodiment of the disclosure, a prosthetic heart valve for replacing a native valve includes a stent having an inflow end, an outflow end, a plurality of cells formed by cell struts, a collapsed condition and an expanded condition. A valve assembly is disposed within the stent. A first cuff is annularly disposed adjacent the stent. A second cuff has a proximal edge facing toward the inflow end of the stent and a distal edge facing toward the outflow end of the stent, the second cuff being annularly disposed about the stent radially outward of the first cuff and radially outward of the stent. A plurality of fingers each has a first end coupled to a corresponding cell of the stent and a free end remote from the first end, the distal edge of the second cuff being coupled to the free ends of the fingers at spaced locations around a circumference of the stent, the free ends of the fingers being spaced radially outward of the corresponding cell in the expanded condition of the stent to position the distal edge of the second cuff radially outward of the corresponding cells of the stent at the spaced locations.

According to another embodiment of the disclosure, a prosthetic heart valve for replacing a native valve includes a stent having an inflow end, an outflow end, a plurality of cells formed by cell struts, a collapsed condition and an expanded condition. A valve assembly is disposed within the stent. A first cuff is annularly disposed adjacent the stent. A second cuff has a proximal edge facing toward the inflow end of the stent and a distal edge facing toward the outflow end of the stent, the second cuff being annularly disposed about the stent and positioned radially outward of the first cuff and radially outward of the stent. A third cuff has a proximal edge facing toward the inflow end of the stent and a distal edge facing toward the outflow end of the stent, the third cuff being annularly disposed about the stent and positioned radially outward of the second cuff. The distal edge of the second cuff is coupled to the stent at first attachment points spaced around a circumference of the stent, and the distal edge of the third cuff is coupled to the distal edge of the second cuff at second attachment points spaced around a circumference of the second cuff.

According to a further aspect of the disclosure, a prosthetic heart valve for replacing a native valve includes a stent extending in an axial direction from an inflow end to an outflow end, the stent having a plurality of cells formed by cell struts, a collapsed condition and an expanded condition. A valve assembly is disposed within the stent. A first cuff is annularly disposed adjacent the stent. A second cuff has a proximal edge facing toward the inflow end of the stent and a distal edge facing toward the outflow end of the stent, the second cuff being annularly disposed about the stent radially outward of the first cuff and radially outward of the stent. The second cuff includes a pleat formed by at least two folds in the second cuff.

According to yet another aspect of the disclosure, a prosthetic heart valve for replacing a native valve includes a stent, a valve assembly, a first cuff, and a second cuff. The stent has an inflow end, an outflow end, a plurality of cells formed by cell stratus, a collapsed condition, and an expanded condition. The valve assembly is disposed within the stent. The first cuff is annularly disposed adjacent the stent. The second cuff has a proximal edge facing toward the inflow end of the stent and a distal edge facing outward the outflow end of the stent. The second cuff is annularly disposed about the stent radially outward of the first cuff and radially outward of the stent. The distal edge includes a plurality of peaks and a plurality of troughs, each trough connecting a pair of adjacent peaks. A distalmost portion of each peak is directly coupled to at least one of the first cuff and the stent.

BRIEF DESCRIPTION OF THE DRAWINGS

Various embodiments of the presently disclosed prosthetic heart valve may be more fully understood with reference to the following detailed description when read with the accompanying drawings, in which:

FIGS. 5A-M are schematic views of alternate embodiments of fingers;

FIGS. 6C-D are schematic developed views of a stent in an expanded condition and having fingers in different circumferential rows of cells;

FIGS. 7A-B are schematic views of an isolated portion of a stent in a collapsed condition and having different fingers;

FIGS. 9A-C are enlarged views of an isolated annulus portion of a stent in a collapsed condition and having different configurations of tapered strut widths;

FIG. 16A is a highly schematic partial side view of an outer cuff with pleats extending in a circumferential direction of the heart valve according to another embodiment of the disclosure, the pleats being shown in a flattened condition;

FIG. 16B is an enlarged cross-sectional view of a group of the circumferential pleats of FIG. 16A taken in a direction transverse to the circumferential direction;

FIG. 16C is a highly schematic partial side view of the outer cuff of FIG. 16A, showing the pleats in a billowed out condition;

DETAILED DESCRIPTION

As used herein in connection with a prosthetic heart valve, the term "inflow end" refers to the end of the heart valve through which blood enters when the valve is functioning as intended, and the term "outflow end" refers to the end of the heart valve through which blood exits when the valve is functioning as intended. As used herein, the term "proximal" refers to the inflow end of a prosthetic heart valve or to elements of a prosthetic heart valve that are relatively close to the inflow end, and the term "distal" refers to the outflow end of a prosthetic heart valve or to elements of a prosthetic heart valve that are relatively close to the outflow end. As used herein, the terms "generally," "substantially," and "about" are intended to mean that slight deviations from absolute are included within the scope of the term so modified. Like numbers refer to similar or identical elements throughout. When used herein in the context of a prosthetic heart valve, or a component thereof, the lengthwise or axial direction refers to a direction parallel to a longitudinal axis passing through the center of the stent or heart valve. When used herein in the context of a prosthetic heart valve, or a component thereof, the circumferential direction refers to a direction extending along the circumference of the prosthetic heart valve.

Figure 1:
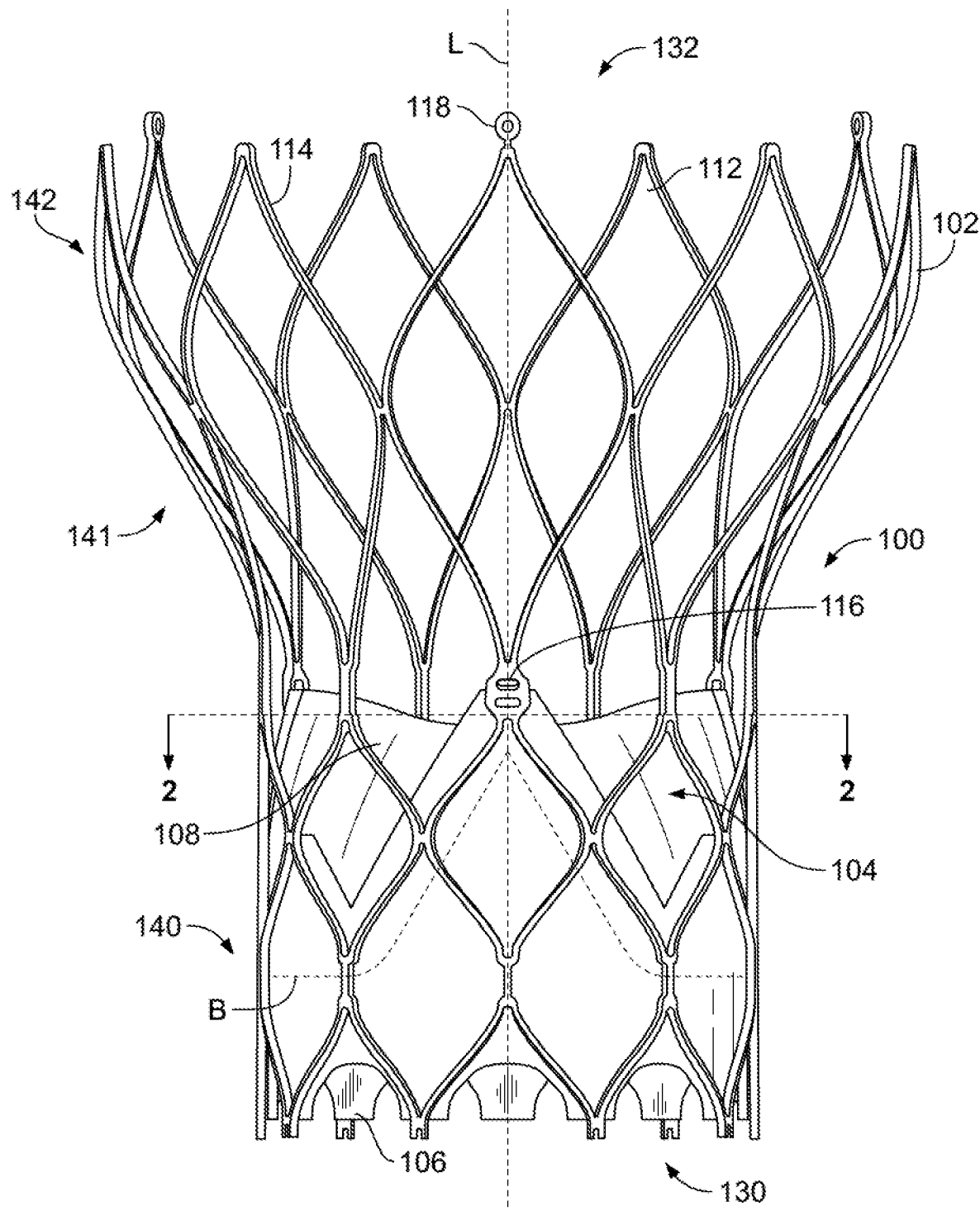
FIG. 1 is a front view of a collapsible prosthetic heart valve according to the prior art shown in an expanded condition.

FIG. 1 shows a collapsible stent-supported prosthetic heart valve 100 according to the prior art, the prosthetic heart valve being shown in an expanded condition. Prosthetic heart valve 100 is designed to replace the function of the native aortic valve of a patient. Prosthetic heart valve 100 includes a stent 102 which serves as a frame for the valve elements. Stent 102 extends along a lengthwise or longitudinal axis L from an inflow or annulus end 130 to an outflow or aortic end 132, and includes an annulus section 140 adjacent inflow end 130 and an aortic section 142 adjacent outflow end 132. Annulus section 140 may be in the form of a cylinder having a substantially constant diameter along its length, and may have a relatively small transverse cross-section in the expanded condition in comparison to the transverse cross-section of aortic section 142. A transition section 141 may taper outwardly from annulus section 140 to aortic section 142. Each of the sections of stent 102 includes a plurality of cells 112 formed by interconnected struts 114. Each cell 112 may include four struts 114 connected together generally in a diamond shape so as to form a cell that may be readily collapsed and expanded. It will be appreciated that a smaller or larger number of struts may be used to form cells having a different shape. The cells 112 in each section of stent 102 may be connected to one another in one or more annular rows around the stent. For example, as shown in FIG. 1, annulus section 140 may have two annular rows of complete cells 112, with the cells in one annular row offset by one-half cell width in the circumferential direction from the cells in the other annular row. Aortic section 142 and transition section 141 may each have one or more annular rows of complete or partial cells 112. The cells in aortic section 142 may be larger than the cells in annulus section 140 so as to better enable prosthetic valve 100 to be positioned within the aortic annulus without the structure of stent 102 interfering with blood flow to the coronary arteries. At least partly due to the shape of cells 112, stent 102 elongates in the direction of longitudinal axis L as the cells collapse when the stent transitions from the expanded condition to the collapsed condition, and shortens in the direction of longitudinal axis L as the stent transitions from the collapsed condition to the expanded condition.

Stent 102 may include one or more retaining elements 118 at outflow end 132, the retaining elements being sized and shaped to cooperate with retaining structures provided on a deployment device (not shown). The engagement of retaining elements 118 with the retaining structures on the deployment device may help maintain prosthetic heart valve 100 in assembled relationship with the deployment device, minimize longitudinal movement of the prosthetic heart valve relative to the deployment device during unsheathing or resheathing procedures, and help prevent rotation of the prosthetic heart valve relative to the deployment device as the deployment device is advanced to the target location and during deployment. One such deployment device is described in U.S. Patent Publication No. 2012/0078352, the entire contents of which are hereby incorporated by reference herein.

Stent 102 may also include a plurality of commissure attachment features 116 for mounting the commissures of the valve assembly to the stent. As can be seen in FIG. 1, each commissure attachment feature 116 may lie at the intersection of four cells 112, two of the cells being adjacent one another in the same annular row, and the other two cells being in different annular rows and lying in end-to-end relationship. Commissure attachment features 116 may be positioned entirely within annulus section 140 or at the juncture of annulus section 140 and transition section 141, and may include one or more eyelets or apertures which facilitate the suturing of the leaflet commissures to stent 102. Stent 102 may be formed as a unitary structure, for example, by laser cutting or etching a tube of a superelastic and/or shape-memory metal alloy, such as a nickel-titanium alloy of the type sold under the designation nitinol. Such a unitary structure may be referred to as a "non-woven" structure in that it is not formed by weaving or winding one or more filaments.

Prosthetic heart valve 100 includes a valve assembly 104 positioned in the annulus section 140 of stent 102. Valve assembly 104 includes a plurality of leaflets 108 that collectively function as a one way valve by coapting with one another, and a cuff 106 positioned on the luminal surface of stent 102 surrounding leaflets 108. As prosthetic heart valve 100 is intended to replace the aortic valve (which ordinarily is a tri-leaflet valve), it is shown in FIG. 1 with three leaflets 108. Adjacent leaflets 108 join one another at leaflet commissures. Each of the leaflet commissures may be sutured to a respective one of the three commissure attachment features 116. Between the leaflet commissures, each leaflet 108 may be sutured to stent 102 and/or to cuff 106 along a leaflet belly B, indicated with broken lines in FIG. 1. Leaflets 108 may be joined to stent 102 and/or to cuff 106 by techniques known in the art other than suturing. Above belly B, leaflets 108 are free to move radially inward to coapt with one another along their free edges. When prosthetic heart valve 100 is implanted in the native aortic valve annulus, blood flows in an antegrade direction from inflow end 130, past leaflets 108, and toward outflow end 132. This occurs when the pressure in the left ventricle is greater than the pressure in the aorta, forcing leaflets 108 to open. When the pressure in the aorta is greater than the pressure in the left ventricle, leaflets 108 are forced closed and coapt with one another along their free edges, blocking blood from flowing through prosthetic heart valve 100 in a retrograde direction from outflow end 132 to inflow end 130. It will be appreciated that prosthetic heart valves according to aspects of the present disclosure may have more or less than the three leaflets 108 and commissure attachment features 116 shown in FIG. 1 and described above.

Although cuff 106 is shown in FIG. 1 as being disposed on the luminal or inner surface of annulus section 140, the cuff may be disposed on the abluminal or outer surface of the annulus section, or may cover all or part of either or both of the luminal and abluminal surfaces of the annulus section. Cuff 106 may be scalloped at the inflow end 130 of stent 102, and may have a zig-zag structure at its outflow end, following certain stent struts 114 up to commissure attachment features 116 and other stent struts closer to the inflow end of the stent at circumferential positions between the commissure attachment features. As is shown in FIG. 1, in one example, the entirety of valve assembly 104, including the leaflet commissures, is positioned in the annulus section 140 of stent 102. When open, leaflets 108 may remain substantially completely within annulus section 140, or they may be designed to extend into transition section 141. In the embodiment shown, substantially the entirety of valve assembly 104 is positioned between the inflow end 130 of stent 102 and commissure attachment features 116, and none of the valve assembly is positioned between the commissure attachment features and the outflow end 132 of the stent.

In operation, prosthetic heart valve 100 described above may be used to replace a native heart valve, such as the aortic valve; a surgical heart valve; or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed condition. The delivery device may be introduced into the patient using any known percutaneous procedure, such as a transfemoral, transapical, or transseptal delivery procedure. Once the delivery device has reached the target site, the user may deploy prosthetic heart valve 100. Upon deployment, prosthetic heart valve 100 expands into secure engagement within the native aortic annulus. When prosthetic heart valve 100 is properly positioned inside the heart, it works as a one-way valve, allowing blood to flow in one direction and preventing blood from flowing in the opposite direction.

Figure 2:
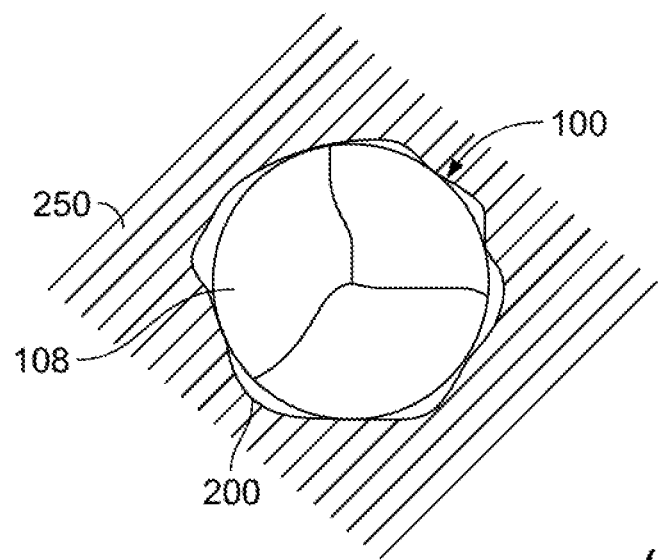
FIG. 2 is a highly schematic transverse cross-sectional view of the prior art prosthetic heart valve implanted in a patient, taken along line 2-2 of FIG. 1.

FIG. 2 is a highly schematic transverse cross-sectional illustration taken along line 2-2 of FIG. 2 and showing prosthetic heart valve 100 with leaflets 108 disposed within native valve annulus 250. As can be seen, the substantially circular annulus section 140 of stent 102 is disposed within a non-circular native valve annulus 250. At certain locations around the perimeter of prosthetic heart valve 100, gaps 200 are formed between the heart valve and native valve annulus 250. Retrograde blood flow through these gaps and around the outside of the valve assembly 104 of prosthetic heart valve 100 can result in PV leak or regurgitation and other inefficiencies which can reduce cardiac performance. Such improper fitment may be due to suboptimal native valve annulus geometry, for example, as a result of the calcification of the tissue of native valve annulus 250 or the presence of unresected native leaflets.

Figure 3A:
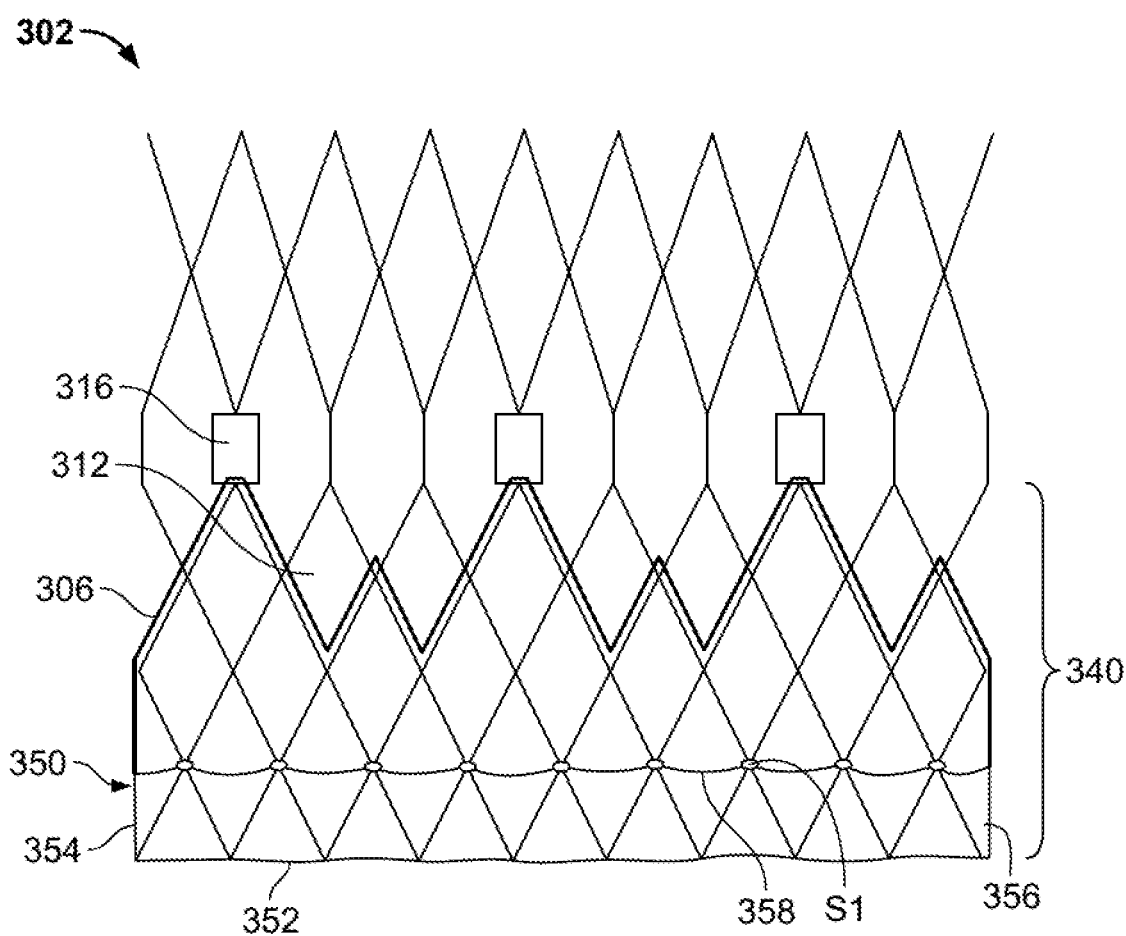
FIG. 3A is a schematic developed view of a stent with an outer cuff in an expanded condition according to an embodiment of the disclosure.

FIG. 3A illustrates the stent 302 of a prosthetic heart valve according to an aspect of the disclosure. Stent 302 may be used in a prosthetic heart valve that is similar or identical to prosthetic heart valve 100 described above, with certain exceptions. For example, the annulus section 340 of stent 302 may include three rows of cells 312 instead of two rows, although in some embodiments stent 302 may include only two rows of cells in the annulus section. Although commissure attachment features 316 of stent 302 are illustrated as open rectangles in FIG. 3A, the commissure attachment features may have a form similar to commissure attachment features 116 shown in FIG. 1, or any other suitable form having any number of rows or columns of eyelets and/or eyelets of different sizes and/or shapes positioned in any arrangement on the commissure attachment feature. A cuff 306 similar or identical to cuff 106 may be positioned on the luminal and/or abluminal surface of stent 302. Rather than a scalloped inflow end as with cuff 106, however, cuff 306 may have a straight inflow end. Cuff 306 may be positioned on the luminal or internal surface of stent 302. In order to help minimize or eliminate PV leak, for example through the gaps 200 shown in FIG. 2, additional material may be coupled to the exterior of stent 302 as an outer cuff 350. In the illustrated example, outer cuff 350 may have a substantially rectangular shape and may be wrapped around the circumference of stent 302 at the inflow end of the stent so as to overlap in the longitudinal direction of the stent with cuff 306. Outer cuff 350 may be a single piece of material having a proximal edge 352, two side edges 354, 356, and a distal edge 358. Preferably, the proximal edge 352 of outer cuff 350 is coupled to stent 302 and/or to inner cuff 306 at or near the inflow end of the stent, for example by a continuous line of sutures (not shown), with the side edges 354 and 356 of the outer cuff joined to one another so that retrograde blood flow entering the space between the outer cuff and the inner cuff cannot pass in the retrograde direction beyond the combined cuffs. In order to allow retrograde blood flow to enter the space between outer cuff 350 and inner cuff 306, the distal edge 358 of the outer cuff may be attached to stent 302 and/or to inner cuff 306 at locations that are spaced apart in the circumferential direction. The distal edge 358 of outer cuff 350 may, for example, be sutured to stent 302 at attachment points S1 located where each cell 312 in the proximalmost row of cells intersects with an adjacent cell in that same row. In the illustrated example, since there are nine cells 312 in the proximalmost row, there are nine separate attachment points S1 at which the distal edge 358 of outer cuff 350 is sutured or otherwise attached to stent 302. Retrograde blood flow around the abluminal surface of stent 302 may enter the pocket or space between outer cuff 350 and inner cuff 306 via the spaces between adjacent attachment points S1. Once retrograde blood flow enters this space, outer cuff 350 may tend to billow outwardly, helping to fill any of gaps 200 between the prosthetic heart valve and native valve annulus 250. Although the foregoing description uses the term "inner" in connection with cuff 306, that is merely intended to indicate that cuff 306 is positioned radially inward of outer cuff 350. Inner cuff 306 may be located either on the luminal or abluminal side of stent 302, or on both sides.

Although described as a single piece of material above, outer cuff 350 may comprise multiple pieces of material that, when joined together, form a similar shape and provide similar function as described above for the outer cuff. Also, rather than being formed of a single substantially rectangular piece of material that is wrapped around the circumference of stent 302, outer cuff 350 may be formed as a continuous annular web without side edges 354, 356. Preferably, outer cuff 350 has an axial height measured from its proximal edge 352 to its distal edge 358 that is approximately half the axial height of a cell 312 in the proximalmost row of cells in stent 302 as measured along the major axis of the cell between two of its apices when the cell is in an expanded condition. However, outer cuff 350 may have other suitable heights, such as the full axial height of a cell 312 in the proximalmost row of cells, or more or less than the full axial height of a cell 312 in the proximalmost row of cells. Still further, although inner cuff 306 and outer cuff 350 are described above as separate pieces of material joined to stent 302 and to each other, the cuffs may be formed integrally with one another from a single piece of material that is wrapped around the proximal edge of the stent, with the distal edge 358 of the outer portion of the cuff joined to the stent and/or to the inner portion of the cuff at attachment points S1 as described above. With this configuration, the proximal edge 352 of outer cuff 350 does not need to be sutured to stent 302, although it still may be preferable to provide such attachment. Inner cuff 306 and outer cuff 350 may be formed of the same or different materials, including any suitable biological material or polymer such as, for example, polytetrafluoroethylene (PTFE), ultra-high molecular weight polyethylene (UHMWPE), polyurethane, polyvinyl alcohol, silicone, or combinations thereof.

Figure 3B:
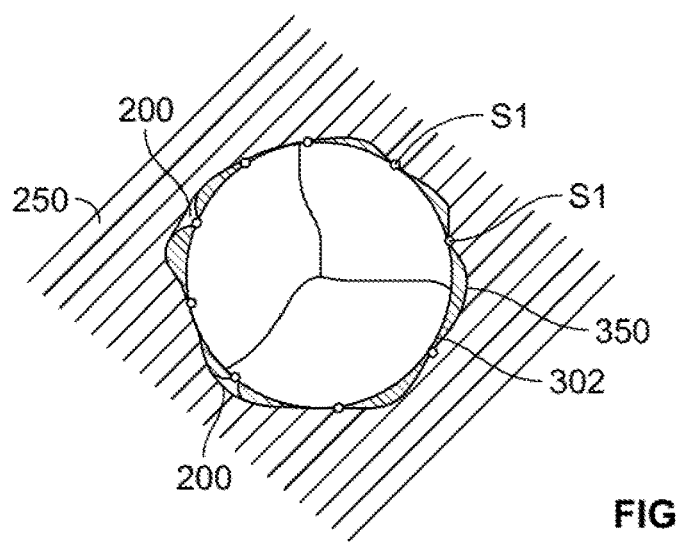
FIG. 3B is a highly schematic transverse cross-sectional view of a prosthetic heart valve including the stent and cuff of FIG. 3A implanted in a patient.

As shown in FIG. 3B, when a prosthetic heart valve including stent 302, inner cuff 306 and outer cuff 350 is implanted in a native valve annulus 250, retrograde blood flow may cause the outer cuff to billow radially outward and fill gaps 200. However, the attachment of the distal edge 358 of outer cuff 350 to stent 302 and/or to inner cuff 306 at attachment points S1 may prevent the outer cuff from billowing outwardly at those points. If any gap 200 is radially aligned with, or nearly radially aligned with, an attachment point S1, outer cuff 350 may not be able to fill that gap. This situation is seen in FIG. 3B near the top left and bottom left of stent 302.

Figure 4A:
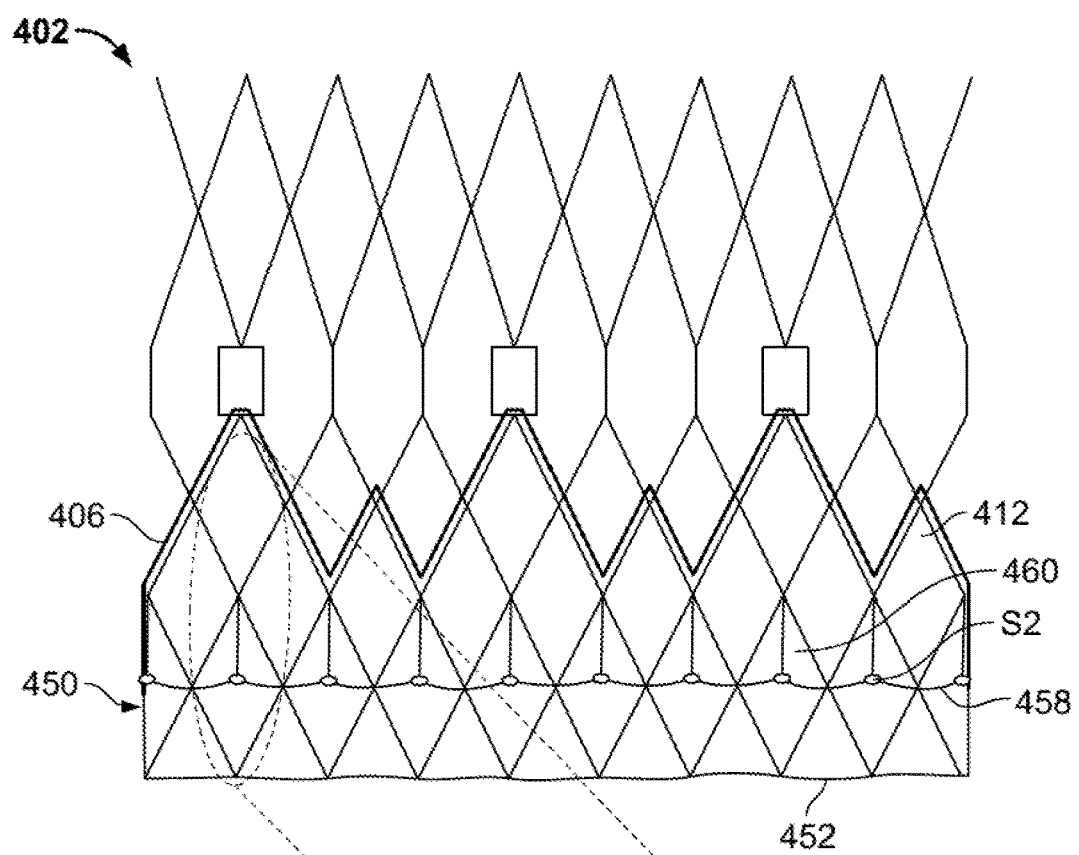
FIG. 4A is a schematic developed view of a stent with an outer cuff and fingers in an expanded condition according to another embodiment of the disclosure.

In order to address the drawback noted above, the prosthetic heart valves of the present disclosure may incorporate features that better enable the cuff of the prosthetic heart valve to fill any gaps that may remain once the heart valve has been implanted in a native valve annulus. A stent 402, inner cuff 406 and outer cuff 450 incorporating one such feature is shown in FIG. 4A. Stent 402, inner cuff 406 and outer cuff 450 each may be similar or identical to stent 302, inner cuff 306 and outer cuff 350, with the exceptions described below. Outer cuff 450 may include a proximal edge 452 that is attached to stent 402 and/or to inner cuff 406 at or near the inflow end of the stent or at other axial positions, for example by a continuous line of sutures (not shown). Outer cuff 450 and inner cuff 406 may together form at least one pocket adapted to receive retrograde blood flow, thereby causing the outer cuff to billow outwardly similarly to outer cuff 350. However, rather than attaching the distal edge 458 of outer cuff 450 to the struts forming cells 412 of stent 402, the distal edge of the outer cuff is attached at different attachment points S2. Attachment points S2 may be provided at the free ends of additional struts or fingers 460 on stent 402.

Fingers 460 are preferably formed integrally with the remainder of stent 402 and are substantially straight, with a first end 462 attached to a cell 412 of the stent, and a second free end 464. For example, if stent 402 is formed by laser cutting a single tube, as described above in connection with stent 102, fingers 460 may also be formed by laser cutting the same tube. Alternatively, fingers 460 may be formed separately and then attached to stent 402, for example by adhesives, sutures, welding, or otherwise. In the embodiment shown in FIGS. 4A-B, the first end 462 of each finger 460 is coupled to a cell 412 in the proximalmost row of cells of stent 402. In particular, the first end 462 of each finger 460 is coupled to its respective cell 412 at the distalmost apex of the cell, with the free end 464 of each finger positioned within the cell, proximal to first end 462. The free end 464 of each finger 460 may terminate in a blunted tip, such as a round (two-dimensional), spherical (three-dimensional) or partially spherical tip. The blunted tip at the free end 464 of each finger 460 may serve as an attachment point S2 for attaching the distal edge 458 of outer cuff 450 to stent 402, for example by a suture. Outer cuff 450 preferably is attached to the free end 464 of finger 460 so that the finger is positioned radially inward of the outer cuff or directly distal to the outer cuff, although the finger may alternately be positioned radially outward of the outer cuff. Fingers 460 are also preferably positioned radially outward of inner cuff 406. Providing a blunted tip at the free end 464 of finger 460 may help to keep the finger from piercing or otherwise damaging native tissue, outer cuff 450 or other components of the prosthetic valve.

Figure 4B:
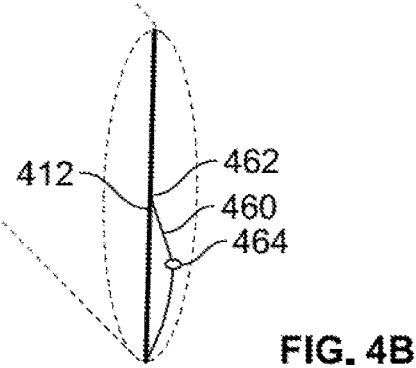
FIG. 4B is an isolated side view of a portion of the stent, outer cuff and a finger of FIG. 4A.

Preferably, fingers 460 are shape set, for example by heat setting, so that in the absence of any applied forces, the free ends 464 of the fingers extend radially outward from the respective cells 412 in which the fingers are positioned, as shown in FIG. 4B. When a prosthetic heart valve incorporating stent 402 and outer cuff 450 is implanted into a native valve annulus in a patient, for example native valve annulus 250, the entire distal edge 458 of outer cuff 450 will be able to expand radially outward into any gaps 200, without the potential limitations described above with respect to the outer cuff 350 of stent 302. In other words, as fingers 460 expand radially outward, their free ends 464 carry with them the distal edge 458 of outer cuff 450. Thus, each attachment point S2 is able to be positioned radially outward of its respective cell 412, which, in turn, allows the distal edge 458 of outer cuff 450 at each attachment point S2 to extend outwardly from stent 402. As a result, retrograde blood flow entering the space between outer cuff 450 and inner cuff 406 will move the entire distal edge 458 of outer cuff 450 outwardly toward the native valve annulus and into gaps 200, even those gaps that may be radially aligned with attachment points S2. Providing shape setting to bias the free ends 464 of fingers 460 radially outward of the respective cells 412 to which they are attached may assist the distal edge 458 of outer cuff 450 to extend into any gaps 200. However, such biasing may not be necessary since the pressure produced as retrograde blood flow enters the space between inner cuff 406 and outer cuff 450 may be sufficient to cause the desired billowing of the outer cuff into gaps 200.

Figure 4C:
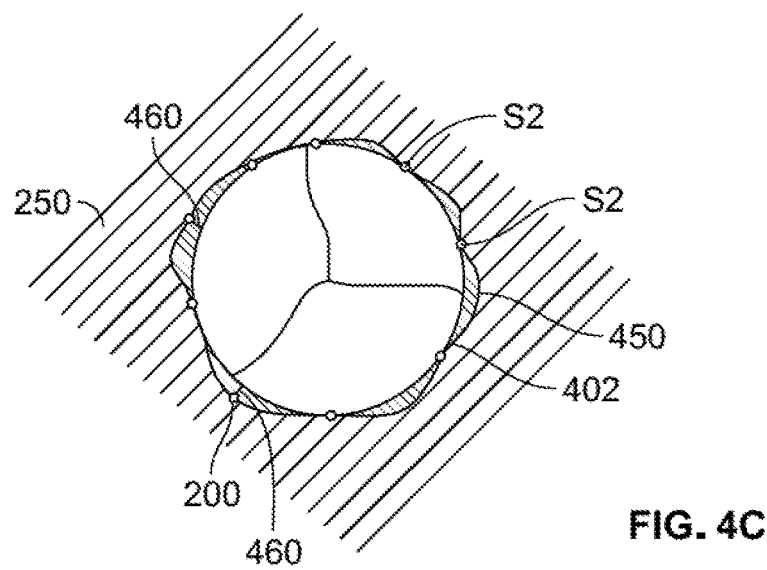
FIG. 4C is a highly schematic transverse cross-sectional view of a prosthetic heart valve including the stent and cuff of FIG. 4A implanted in a patient.

Each finger 460 may have a similar cross-sectional shape and thickness as the struts forming the remainder of stent 402. However, it may be beneficial for fingers 460, or at least a portion of the fingers, to be substantially thinner, narrower and/or weaker than the struts forming the remainder of stent 402. For example, if fingers 460 are very thick, wide or otherwise stiff or strong compared to the remainder of stent 402, the force exerted as the free ends 464 of fingers 460 are biased radially outward against native annulus 250 could cause the inflow end of stent 402 to deform, which may be undesirable. Where fingers 460 are not biased outwardly, the pressure produced as retrograde blood flow enters the space between inner cuff 406 and outer cuff 450 may be insufficient to deflect stiff and strong fingers 460 outwardly into gaps 200. By forming fingers 460 with a cross-sectional thickness and/or width that is less than the cross-sectional thickness and/or width, respectively, of the struts forming the remainder of stent 402, less force may be required to deflect the fingers radially outward and these potential problems can be avoided. In the embodiment of FIGS. 4A-B in which fingers 460 are coupled to the remainder of stent 402 at only one point, such a concern may be negligible. However, if fingers 460 are configured to attach to cells 412 at multiple points, for example to multiple struts of a cell, it may be more important to form the fingers with a smaller cross-sectional thickness and/or width compared to the struts forming the remainder of stent 402 so as to require less deflection force. The amount of force required to deflect fingers 460 outwardly is preferably such that, when a cell 412 of stent 402 directly abuts native valve annulus 250 with no gap 200, the finger 460 associated with that cell 412 is positioned in substantially the same plane as the four struts forming that cell and does not exert a force deforming the stent, but when a cell is spaced from the native valve annulus so as to leave a gap 200, the finger associated with that cell deflects radially outward accompanied by the distal edge 458 of outer cuff 450 to fill the gap. This arrangement is illustrated in FIG. 4C, which shows that the fingers 460 adjacent native valve annulus 250 are substantially aligned within the circumference of stent 402 (as shown by the positions of corresponding attachment points S2), whereas the fingers 460 adjacent gaps 200 extend into the gaps, bringing the distal edge 458 of outer cuff 450 radially outward into those gaps to help prevent PV leak.

Figure 5A:
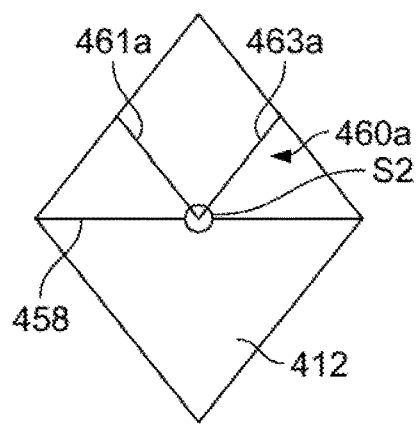

Although fingers 460 are described as singular struts, the fingers may be formed in a number of alternate configurations, some of which are shown in FIGS. 5A-M. FIG. 5A shows a finger 460a within a cell 412 in the proximalmost row of stent 402 that includes two struts that together form a "V" shape. In particular, rather than a single strut attached to the distalmost apex of cell 412 as in FIGS. 4A-B, finger 460a is formed by two struts 461a, 463a. Strut 461a has a first end attached to one distalmost strut of cell 412, and strut 463a has a first end attached to the other distalmost strut of cell 412, with the other ends of struts 461a and 463a being coupled to one another to form a free end of finger 460a. The "V" shape of finger 460a may help limit its lateral movement (i.e., in the circumferential direction). Further, the "V" shape of finger 460a provides a convenient and secure attachment point S2 for attaching the distal edge 458 of outer cuff 450 to finger 460a, such as by a suture. In particular, a suture may loop around finger 460a at the point at which struts 461a, 463a connect to one another, making it difficult for the suture to slide with respect to the finger.

Figure 5B:
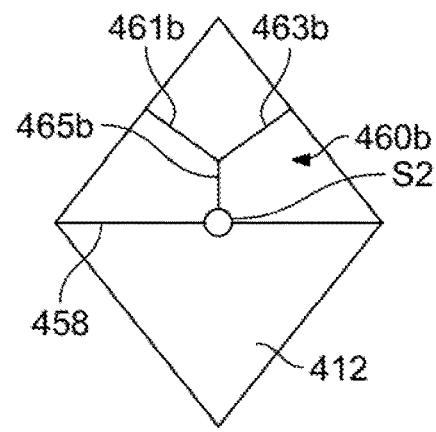

FIG. 5B shows a finger 460b within a cell 412 in the proximalmost row of stent 402 that combines the "V" shape finger 460a of FIG. 5A with the finger 460 of FIGS. 4A-B. In other words, finger 460b includes two struts 461b, 463b that together form a "V" shape. Strut 461b has a first end attached to one strut of cell 412, and strut 463b has a first end attached to an adjacent strut of cell 412, with the other ends of struts 461b, 463b being coupled to one another to form a "V" shape. A third strut 465b is attached at one end to the intersection of struts 461b and 463b and extends axially to a free end positioned within cell 412. The distal edge 458 of outer cuff 450 is attached to the free end of strut 465b at attachment point S2. Similar to finger 460, the free end of strut 465b may include a blunted tip which may help avoid damaging native tissue, outer cuff 450 or other components of the prosthetic heart valve, and which may further provide a structure for securing a suture to the free end of strut 465b. Finger 460b may provide a balance between the attributes of fingers 460 and 460a—flexibility and/or formability provided by straight strut 465b, together with lateral stiffness provided by struts 461b and 463b.

Figure 5C:
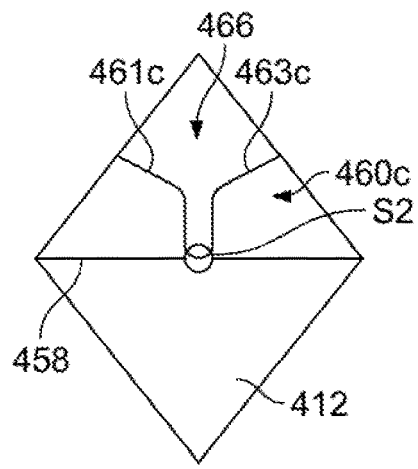

FIG. 5C shows a finger 460c within a cell 412 in the proximalmost row of stent 402 that is similar to the "V"-shaped finger of FIG. 5A. Finger 460c may include a first strut 461c coupled to one strut of cell 412 and a second strut 463c coupled to an adjacent strut of cell 412. However, struts 461c and 463c are not so straight as to form a sharp "V"-shaped angle between them, as in finger 460a. Rather, a first portion of strut 461c closest to its attachment to cell 412 and a first portion of strut 463c closest to its attachment to cell 412 are substantially straight. Second portions of struts 461c and 463c remote from their attachments to cell 412 curve away from one another to form portions that are substantially parallel to one another with a narrow gap 466 therebetween. The second portions of struts 461c and 463c finally join one another in a "U"-shaped connection to form a free end of finger 460c. Similar to finger 460a, a suture may couple the distal edge 458 of outer cuff 450 securely to finger 460c, with narrow gap 466 making it difficult for the suture to slide or otherwise move with respect to finger 460c and/or outer cuff 450.

Figure 5D:
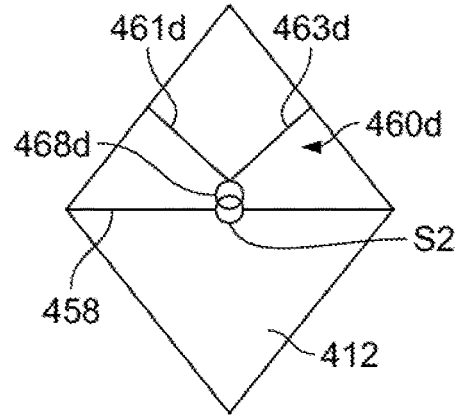

FIG. 5D shows a finger 460d that is identical to finger 460a with one additional feature. An eyelet 468d is provided at the "V"-shaped intersection of struts 461d and 463d. Rather than coupling a suture at the "V"-shaped intersection, the suture may be positioned through eyelet 468d to provide secure fixation. It should be understood that similar eyelets may be provided in any of the other fingers described herein, and all of the fingers described herein may optionally be shape set so as to have free ends that, in the absence of applied forces, are biased radially outward with respect to the cell 412 in which the finger is positioned.

FIG. 5E shows a finger 460e within a cell 412 in the proximalmost row of stent 402 that is similar to the "V"-shaped finger of FIG. 5A. However, rather than having struts connected to the distalmost struts of cell 412, finger 460e includes a first strut 461e having one end coupled to the distalmost strut on one lateral side of the cell and a second strut 463e having one end coupled to the proximalmost strut on the same lateral side of the cell. The other ends of struts 461e and 463e are coupled to one another to form a free end of finger 460e. In the collapsed condition of stent 402, struts 461e and 463e will tend to align substantially colinearly with one another as a single long strut extending in the axial direction of the stent. Accordingly, cell 412 may be able to collapse to a smaller circumferential size than the cells incorporating fingers 460a-460d. Because finger 460e is substantially straight in the collapsed condition, its free end does not form a sharp "V" in the expanded condition, but rather forms a more rounded configuration. Therefore, the free end of finger 460e may include an eyelet or other feature for suturing the finger to the distal edge 458 of outer cuff 450 so that the suture does not slide along struts 461e or 463e as stent 402 is expanded or during use of the implanted prosthetic heart valve.

FIG. 5F shows a pair of fingers 460f within a cell 412 in the proximalmost row of stent 402. Fingers 460f are similar to finger 460e of FIG. 5E, but one finger is attached to the struts on one lateral side of cell 412 and the other finger is attached to the struts on the opposite lateral side of the cell. As with finger 460e, the struts forming each of fingers 460f will tend to align substantially colinearly with one another when stent 402 is in the collapsed condition and will form a more rounded free end in the expanded condition of the stent. The free ends of fingers 460f provide two points at which the distal edge 458 of outer cuff 450 may be attached to stent 402. Similar to finger 460e, each of fingers 460f may include an eyelet or other feature at its free end to help secure outer cuff 450 to the finger.

FIG. 5G shows a finger 460g within a cell 412 in the proximalmost row of stent 402 that is similar to the "V"-shaped finger of FIG. 5A. However, rather than having both of the struts of the finger coupled at similar positions along the cell struts, finger 460g has a first strut 461g coupled to one strut of cell 412 at a point relatively close to the distalmost apex of the cell, and a second strut 463g coupled to another strut of the cell at a point farther from the distalmost apex of the cell. As a result of this configuration, the points at which struts 461g and 463g connect to the cell struts will not interfere with one another as stent 402 is collapsed. Therefore, it may be possible to collapse a stent 402 incorporating fingers 460g to a smaller circumferential size than can be achieved in a stent incorporating fingers 460a. It will be appreciated that one of struts 461g and 463g may be connected at or near the midpoint of a cell strut as long as the other one of struts 461g and 463g is connected at a different position along its cell strut so that the points of attachment of struts 461g and 463g to the struts of cell 412 do not interfere with one another as stent 402 is collapsed.

FIG. 5H shows a finger 460h within a cell 412 in a proximalmost row of stent 402. Finger 460h includes a first strut 461h having one end attached to the distalmost strut on one lateral side of cell 412, and a second strut 463h having one end attached to the proximalmost strut on the opposite lateral side of the cell. The opposite end of strut 461h has a "V"-shaped bend pointing in the proximal direction and the opposite end of strut 463h has a "V"-shaped bend pointing in the distal direction, with the two "V" shaped bends being connected to one another. As with finger 460g of FIG. 5G, the points at which struts 461h and 463h of finger 460h attach to the struts of cell 412 are offset from one another in the longitudinal or axial direction of the cell, and therefore will not interfere with one another when stent 402 is placed in the collapsed condition. Furthermore, as finger 460h forms two side-by-side "V" shapes, each "V" shape expands to a lesser extent than the finger 460g of FIG. 5G when stent 402 is placed in the expanded condition. As a result, less strain is produced in finger 460h as stent 402 is expanded than is generated, for example, at the free end of finger 460g of FIG. 5G.

FIG. 5I shows a finger 460i within a cell 412 in the proximalmost row of stent 402 that is similar to the "V"-shaped finger of FIG. 5A, but in which struts 461i and 463i are attached to the proximalmost struts of the cell with the "V"-shaped free end of the finger pointing distally, rather than being attached to the distalmost struts of the cell with the "V"-shaped free end of the finger pointing proximally. With the distal edge 458 of outer cuff 450 connected to the free end of finger 460i, struts 461i and 463i will be positioned between the body of stent 402 and the outer cuff. In this position, outer cuff 450 may protect finger 460i from any calcium buildup that may occur following implantation of the prosthetic heart valve in a patient. In a preferred arrangement, the free end of finger 460*i* may include an eyelet or other structure for suturing the distal edge 458 of outer cuff 450 to the finger to prevent the sutures from sliding proximally along either one of struts 461*i* or 463*i*.

During the process of implanting a prosthetic heart valve in a native valve annulus, the position of the prosthetic heart valve may slip slightly from the desired position, whereupon calcium deposits in or around the native valve annulus may contact one or more fingers 460 and deform same in the circumferential or axial direction of stent 402. This deformation of any of fingers 460 may affect the functioning of the finger and may induce additional strain therein which could be detrimental to the long term functioning of the prosthetic heart valve. It therefore may be desirable to more securely support the free ends of fingers 460 to help prevent them from being damaged or deformed during valve implantation.

FIG. 5J shows one configuration for supporting the free end of a finger 460*j* that is substantially the same as the "V"-shaped finger of FIG. 5A. Finger 460*j* includes struts 461*j* and 463*j* each having one end attached to a distalmost strut of cell 412 and their other ends coupled to one another to form a "V" shape pointing in the proximal direction. A third strut 465*j* is attached at one end to the intersection of struts 461*j* and 463*j* and at the other end to the proximalmost apex of cell 412 or to one of the proximalmost struts of the cell. By anchoring the free end of finger 460*j* to cell 412, the finger is less likely to be deformed or damaged by any calcium deposits during implantation of the prosthetic heart valve.

FIG. 5K shows another configuration for supporting the free end of a finger 460*k* that is substantially similar to finger 460*j*. Finger 460*k* includes struts 461*k* and 463*k*, each having a first end attached to a distalmost strut of cell 412, and second ends coupled to one another to form a "V" shape pointing in the proximal direction. A third strut 465*k* is attached at one end to the intersection of struts 461*k* and 463*k* and at the other end to the proximalmost apex of cell 412 or to one of the proximalmost struts of the cell. Rather than being substantially straight as in the embodiment of FIG. 5J, which may form a relatively stiff structure that limits the outward deflection of the fingers, strut 465*k* has a serpentine configuration which is less stiff, and which may be able to elongate so as to not impede the outward deflection of finger 460*k*. Nonetheless, by anchoring the free end of finger 460*k*, strut 465*k* may help prevent any deformation or damage to the finger as the prosthetic heart valve is implanted.

FIG. 5L shows yet another configuration for supporting the free end of a finger 460*l* that is substantially similar to finger 460*j*. Finger 460*l* includes struts 461*l* and 463*l*, each having a first end attached to a distalmost strut of cell 412, and second ends coupled to one another to form a "V" shape pointing in the proximal direction. A third strut 465*l*1 is attached at one end to strut 461*l* and at the other end to a proximalmost strut of cell 412, and a fourth strut 465*l*2 is connected at one end to strut 463*l* and at the other end to another proximalmost strut of cell 412. Together, struts 465*l*1 and 465*l*2 support the free end of finger 460*l* and help prevent it from being damaged, such as by calcium deposits during valve implantation. Rather than forming struts 465*l*1 and 465*l*2 as substantially straight struts as illustrated in FIG. 5L, those struts may be formed with a serpentine shape in order to reduce the overall stiffness of the structure and not interfere with the proper operation of fingers 460*l*.

FIG. 5M shows another configuration for supporting the free end of a finger 460*m* that is substantially similar to finger 460*j*. Finger 460*m* includes struts 461*m* and 463*m*, each having a first end attached to a distalmost strut of cell 412, and second ends coupled to one another to form a "V" shape pointing in the proximal direction. A third strut 465*m*1 has one end connected to strut 461*m* at point m and a second end connected to the same strut of cell 412 to which strut 461*m* is connected, but at a spaced distance proximal of that connection. A fourth strut 465*m*2 has one end connected to strut 463*m* at point m' and a second end connected to the same strut of cell 412 to which strut 463*m* is connected, but at a spaced distance proximal of that connection. The structure shown in FIG. 5M results in a two-phase expansion of finger 460*m*. As stent 402 begins to expand, the struts of cell 412 will begin to move away from struts 461*m* and 463*m*, respectively, and connection points m and m' will move away from one another. This relative movement will continue until struts 465*m*1 and 465*m*2 are fully expanded, at which juncture the end portions of finger 460*m* connected to the struts of cell 412 (i.e., the portion of strut 461*m* between point m and the cell strut, and the portion of strut 463*m* between point m' and the cell strut) will no longer be able to move relative to the cell struts. However, upon continued expansion of stent 402, point m will continue to move away from point m' so as to form a dog leg in strut 461*m* and a dog leg in strut 463*m*. Hence, in the fully expanded condition of stent 402, finger 460*m* does not have a "V" shape with straight sides as in fingers 460*j*, 460*k* and 460*l* described above.

Figure 5N:
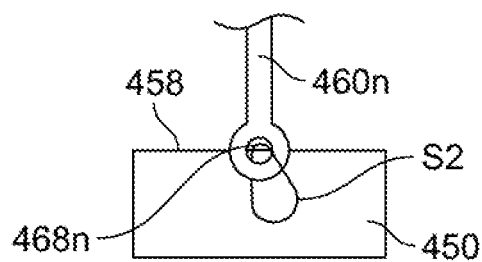
FIGS. 5N-O are schematic views of alternative shapes for free ends of fingers.
Figure 5O:
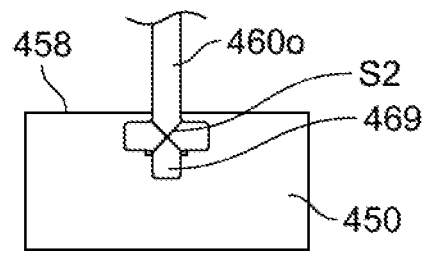

FIG. 5N shows an enlarged view of a finger 460*n* with an eyelet 468*n* at its free end. Finger 460*n* may generally take the form of finger 460 or 460*b*, but includes eyelet 468*n* at its free end to help secure the distal end 458 of outer cuff 450 to the finger, similar to the eyelet 468*d* provided on finger 460*d*. Rather than using an eyelet, the free end of a finger 460*o* may be provided with a cruciform structure 469, such as the structure shown in FIG. 5O, with two lateral projections extending in the circumferential direction, and a third axial projection extending at a right angle to the two lateral projections. A suture coupling the distal edge 458 of outer cuff 450 to finger 460*o* may be wrapped around the projections of the cruciform structure 469, for example in an "X" pattern, to help secure the assembly together.

Figure 5P:
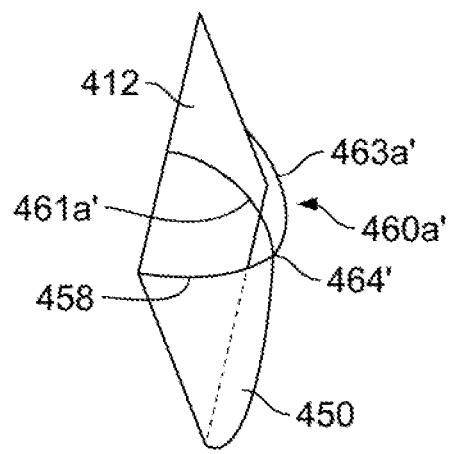
FIG. 5P is a schematic perspective view of a variant of the finger of FIG. 5A.

FIG. 5P shows a variant 460*a*' of the finger 460*a* shown in FIG. 5A. Rather than having substantially straight struts 461*a* and 463*a* that extend from cell 412 at a constant angle when stent 402 is in the expanded condition, each of struts 461*a*' and 463*a*' (or a portion of the struts adjacent the free end 464' of finger 460*a*') may turn back toward the stent either with a gradual smooth curve or with a more pronounced dog leg. This modification may be such that the free end 464' of finger 460*a*' extends along an axis that is parallel to the longitudinal axis of stent 402 in the expanded condition. In addition to the blunt tip on finger 460*a*', this modification may help reduce the risk of the free end 464' of finger 460*a*' piercing or otherwise damaging the native tissue near the valve annulus or possibly damaging the cuff material near the distal edge 458 thereof. Although shown as a modification to the finger of FIG. 5A, this modification may be applied to each of the fingers shown in FIGS. 5B-O, as well as to any of the other such fingers described herein.

Although in the foregoing description of the various embodiments of fingers 460 the distal edge 458 of outer cuff 450 is described as being connected to the free end of the finger, that is not necessarily the case. The distal edge 458 of cuff 450 may be connected to fingers 460 anywhere along the length of their struts 461 and 463. Moreover, while aperture or eyelets for attaching the free edge 458 of outer cuff 450 to fingers 460 are described as being positioned at the free ends of the fingers, those apertures or eyelets may be positioned at any position along the length of struts 461 and 463 at which it is desired to attach the free edge of the outer cuff.

Figure 6A:
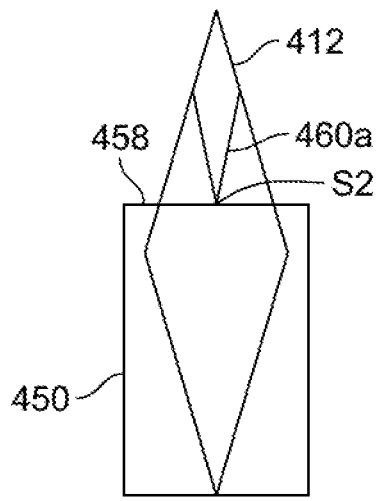
FIGS. 6A-B are schematic views of the finger of FIG. 5A in collapsed and expanded conditions, respectively.
Figure 6B:
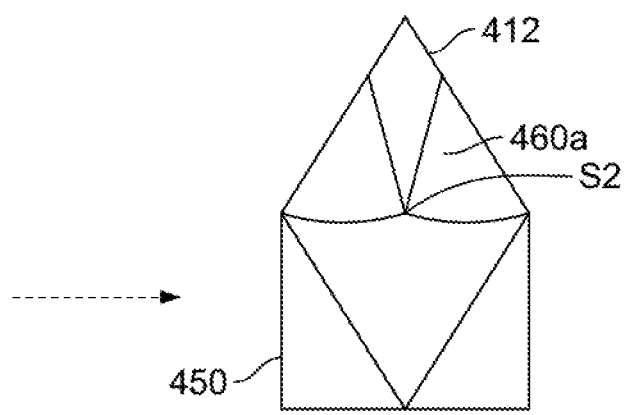

FIGS. 6A-B show additional benefits of using the fingers described herein. FIG. 6A shows the finger 460a of FIG. 5A attached to the distal edge 458 of outer cuff 450 when the stent 402, including cell 412, is in a collapsed condition. Because outer cuff 450 is coupled to stent 402 along the proximal edge of the outer cuff, as well as at select points S2 along the distal edge 458 of the outer cuff, the outer cuff may be relatively taut in the axial direction when stent 402 is in the collapsed condition. This may provide for reduced loading forces when loading a prosthetic heart valve incorporating stent 402 and outer cuff 450 into a delivery device. As stent 402 transitions to the expanded condition shown in FIG. 6B, for example upon being released from the delivery device, outer cuff 450 becomes less taut in the axial direction compared to FIG. 6A. The extra slack in outer cuff 450 in the expanded condition may provide an increased ability for retrograde blood flow around the abluminal surface of stent 402 to make outer cuff 450 billow outwardly, providing for increased mitigation of PV leak.

As noted previously, fingers 460 may be located in the proximalmost annular row x of cells 412 of stent 402, as shown in FIG. 6C. Depending on the size of cells 412, the axial length of outer cuff 450 and other considerations, such location will place fingers 460 in an appropriate location relative to the native valve annulus to enable the outer cuff 450 of the implanted heart valve to mitigate PV leak.

Notwithstanding the foregoing, there may be circumstances in which it is preferable to locate fingers 460 at a different position relative to stent 402. For example, it may be desirable to employ a relatively deep outer cuff 450, i.e., one in which distal edge 458 is positioned closer to commissure attachment features 416. In such event, the distal edge 458 of outer cuff 450 may be located at a position at which any reasonably sized fingers 460 in the proximalmost row x of cells 412 are unable to be attached to the distal edge of the outer cuff, or such fingers may be ineffective in urging the distal edge of the outer cuff radially outward and away from the remainder of stent 402. In that circumstance, it may be more appropriate to locate fingers 460 in the next adjacent annular row y of cells 412, as shown in FIG. 6D. By locating fingers 460 in row y of cells 412, the free ends of the fingers will be positioned farther from the inlet end of stent 402, and therefore will be more appropriately positioned for attachment to the distal edge 458 of outer cuff 450 in those situations in which an outer cuff with a greater axial length is desired. The positioning of fingers 460 is not limited to the proximalmost row x of cells 412 or the next adjacent row y of cells. Rather, fingers 460 may be positioned in any annular row of cells 412 of stent 402 in which they will be most effective. Moreover, fingers 460 need not all be positioned in the same annular row of cells 412. Thus, for example, in certain circumstances it may be beneficial to position one group of fingers 460 in a first annular row of cells 412 and another group of fingers in a second annular row of cells.

In addition to the axial length of outer cuff 450, there may be other considerations that dictate the positions at which fingers 460 are connected to stent 402. For example, when a prosthetic heart valve incorporating inner cuff 406 and outer cuff 450 is implanted in a native valve annulus, the pressure that builds between the cuffs from retrograde blood flow may tend to urge the struts at the proximal end of stent 402 radially inward, away from the native valve annulus, while at the same time urging the fingers 460 of the prosthetic heart valve radially outward against the native valve annulus. The inward deflection of the proximal end of stent 402 relative to fingers 460 results in a strain at the points at which the struts 461 and 463 of fingers 460 join the cell struts. As the pressure buildup between the cuffs occurs with each cardiac cycle, the strain induced in stent 402 occurs countless times during the use of the prosthetic heart valve and could result in premature failure of the stent. Positioning fingers 460 more distally on stent 402 may reduce the strain at these connection points. That is, since the inward deflection of stent 402 progressively diminishes moving away from the inlet end of the stent, by positioning fingers 460 farther from the inlet end of the stent, there will be less movement of the stent at the points at which struts 461 and 463 of the fingers join the cell struts. As a result of this lesser movement, the amount of strain induced in stent 402 at those connection points may be significantly reduced or eliminated.

FIG. 7A illustrates the finger 460e of FIG. 5N within cell 412 in a collapsed condition, for example during laser cutting of stent 402 from a tube. Cell 412 may be formed of four struts 414a-d. FIG. 7A shows that the close spacing between strut 414a and strut 414b may provide a relatively small area from which finger 460e may be laser cut. By increasing this spacing, for example as shown in FIG. 7B in which the distal ends of struts 414a' and 414b' are spaced farther apart such that struts 414a' and 414b' are nearly parallel to one another, a larger area between struts 414a' and 414b' may be formed. In other words, the angle between struts 414a' and 414b' may be smaller than the angle between struts 414a and 414b in the collapsed condition, and may approach a zero degree angle or parallel configuration. This additional area may provide more material initially from which finger 460e' may be laser cut. Thus, the configuration of struts 414a'-d' shown in FIG. 7B may allow finger 460e' to be formed with a greater width compared to finger 460e, which may reduce the likelihood of finger 460e' breaking or otherwise becoming disconnected from stent 402. Despite the difference in geometries between the struts 414a-d shown in FIG. 7A and the struts 414a'-d' shown in FIG. 7B, the cells formed by these respective struts may be nearly identical to one another when in the expanded condition, with the main exception being the narrower width of finger 460e compared to finger 460e'.

The presence of fingers 460e (or any of fingers 460-460f described above) prevents the cells 412 in which the fingers are located from fully collapsing in the collapsed condition of stent 402. That is, in the collapsed condition of cells that do not include a finger 460 (and that do not include components of a valve assembly), strut 414b is able to lie immediately adjacent strut 414a, and strut 414d is able to lie immediately adjacent strut 414c. This full collapsing of cells 412 plainly is not possible for the cells containing a finger 460. As a result, stents 402 incorporating fingers 460 will tend to have a larger circumference in the collapsed condition in the annulus section in which the fingers are incorporated than stents that do not incorporate such fingers, and this larger circumference may make it more difficult to load the collapsed prosthetic heart valve into a delivery device. Moreover, the presence of an inner cuff and valve leaflets within the interior of stent 402 also makes it difficult to collapse the cells 412 in the annulus section of the stent sufficiently to enable loading of the valve into the delivery device. Accordingly, any reduction in the circumference of the prosthetic heart valve in the collapsed condition, particularly in the annulus section of the valve, would be desirable.

Figure 8A:
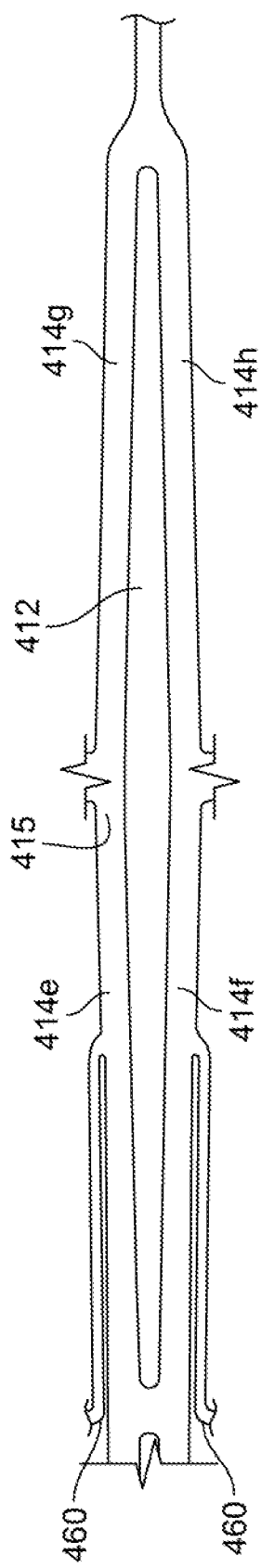
FIG. 8A is an enlarged view of an isolated annulus portion of a stent in a collapsed condition and having conventional strut widths.
Figure 8B:
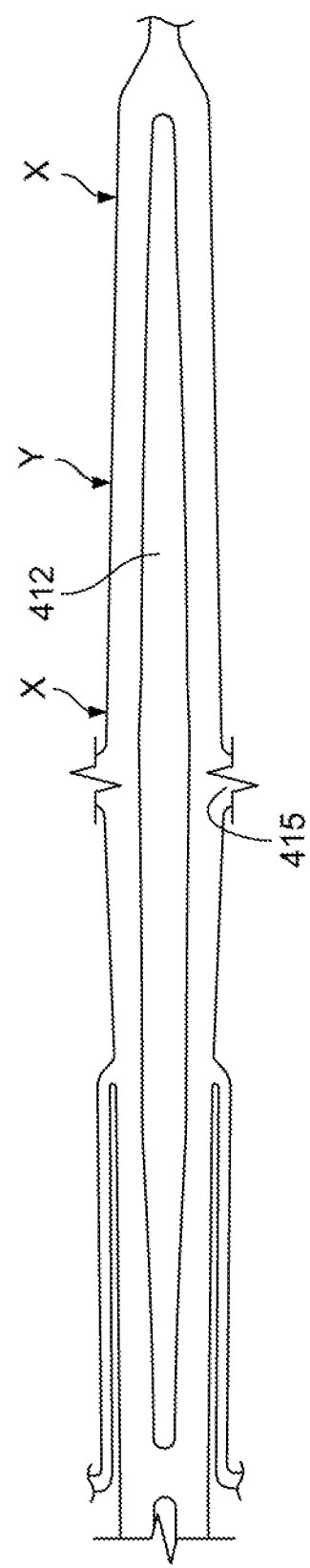
FIG. 8B is an enlarged view of an isolated annulus portion of a stent in a collapsed condition and having tapered strut widths.

One technique for reducing the collapsed circumference of the prosthetic valve in the region of fingers 460 is to taper the width of the struts forming the cells in the annulus section of the stent. An example of this technique is illustrated in FIGS. 8A-B. FIG. 8A shows a collapsed cell 412 of stent 402 in the annulus section of the stent. Cell 412 is formed from struts 414e, 414f, 414g and 414h. Struts 414e and 414f each form a part of another cell incorporating a finger 460, while struts 414g and 414h do not. As shown, the struts forming cell 412 are not tapered. Rather, the struts have a substantially constant width from one end at a longitudinal apex of the cell to another end at an ancon 415 at which cell 412 joins a next adjacent cell.

FIG. 8B illustrates a cell 412 in which the cell struts in the annulus section of the stent have been tapered. More particularly, each of struts 414e', 414f', 414g' and 414h' has been tapered in a region between the ends of the strut. Preferably, the struts may be tapered by an amount sufficient to reduce the mass of the stent without significantly impairing its strength. In a preferred embodiment, the width of the struts in the tapered region may be reduced by about 10% to about 90%, preferably by about 20% to about 55%, compared to the non-tapered regions. The portion of the struts having a tapered width should have a length of between about 20% and about 100% of the length of the strut, with the narrowest portion of the taper having a length of between about 5% and about 50% of the length of the strut. It will be appreciated that the width of the struts may not be narrowed at either end of the strut, i.e., near the axial apices of the cell 412 or in the regions of the struts adjacent ancons 415. Thus, in a preferred arrangement, the tapering of the struts begins at a spaced distance from the ends of the struts.

It is generally known that the radial force exerted by the stent on the native valve annulus is important for holding a valve in place once implanted. Without wishing to be held to any particular theory, it is believed that the portions of the stent most important to radial force generation are at the ends of the cell struts at which one cell joins an adjacent cell (that is, where the apex of a cell in one annular row joins the apex of a cell in an adjacent annular row, or at the ancons where adjacent cells in an annular row join one another). In order to not diminish the radial force generated at these locations, it may be preferable to avoid tapering of the struts at their ends.

There are various ways in which the width of the stent struts can be tapered to achieve a reduced width. Three such arrangements are shown in FIGS. 9A-C. In the FIG. 9A embodiment, the struts taper gradually and continuously from constant-width portions at the ends of the struts until reaching a minimum width. In the FIG. 9B embodiment, on the other hand, the struts narrow rapidly from a constant-width portion at one end of the strut to a reduced width which is maintained along an intermediate portion of the strut until widening again to a constant-width portion of the other end of the strut. It will be appreciated that the width of the struts in the FIG. 9B embodiment has not been narrowed as much as in the FIG. 9A embodiment. The FIG. 9C embodiment is similar to that of FIG. 9A, but the width of the struts has been narrowed to a lesser extent. Any other technique for achieving stent struts that are narrowed in an intermediate portion thereof are contemplated herein. In that regard, while the embodiments shown in FIGS. 9A-C taper the stent struts in a symmetrical center of the strut, that need not be the case. Rather, the stent struts may be tapered at any single location or multiple locations along their length at which it is desired to reduce the bulk of the stent.

In some embodiments, the tapering of struts 414 described above may be performed only on the struts forming the cells 412 in which a finger 460 is located. However, to accommodate the inner cuff and valve leaflets within the interior of stent 402, it is preferable to taper each of the struts in the annulus section of the stent. Thus, for example, for prosthetic heart valves having two full rows of cells 412 between the inlet end of stent 402 and commissure attachment features 416, four circumferential rows of struts 414 may be tapered. For prosthetic heart valves having one full row of cells 412 and one half row of cells between the inlet end of stent 402 and commissure attachment features 416, as in FIGS. 9A-C, three circumferential rows of stent struts 414 may be tapered.

In addition to tapering the struts forming cells 412, it also may be desirable to taper the struts forming fingers 460. For example, for fingers 460 having a particular non-tapered strut width, the strut width may be tapered so that the tapered width is reduced by about 10% to about 90% compared to the non-tapered width, preferably by about 10% to about 35% compared to the non-tapered width. The tapering of the strut width in fingers 460 further diminishes the mass in the annulus section of stent 402 to enhance the ability of the stent to collapse to a small circumference.

Figure 10A:
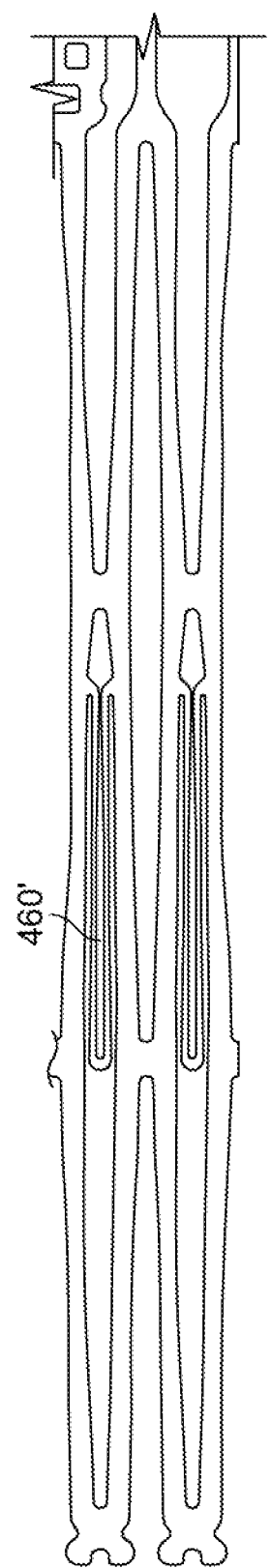
FIG. 10A is an enlarged view of an isolated annulus portion of a stent in a collapsed condition and having elongated fingers.
Figure 10B:
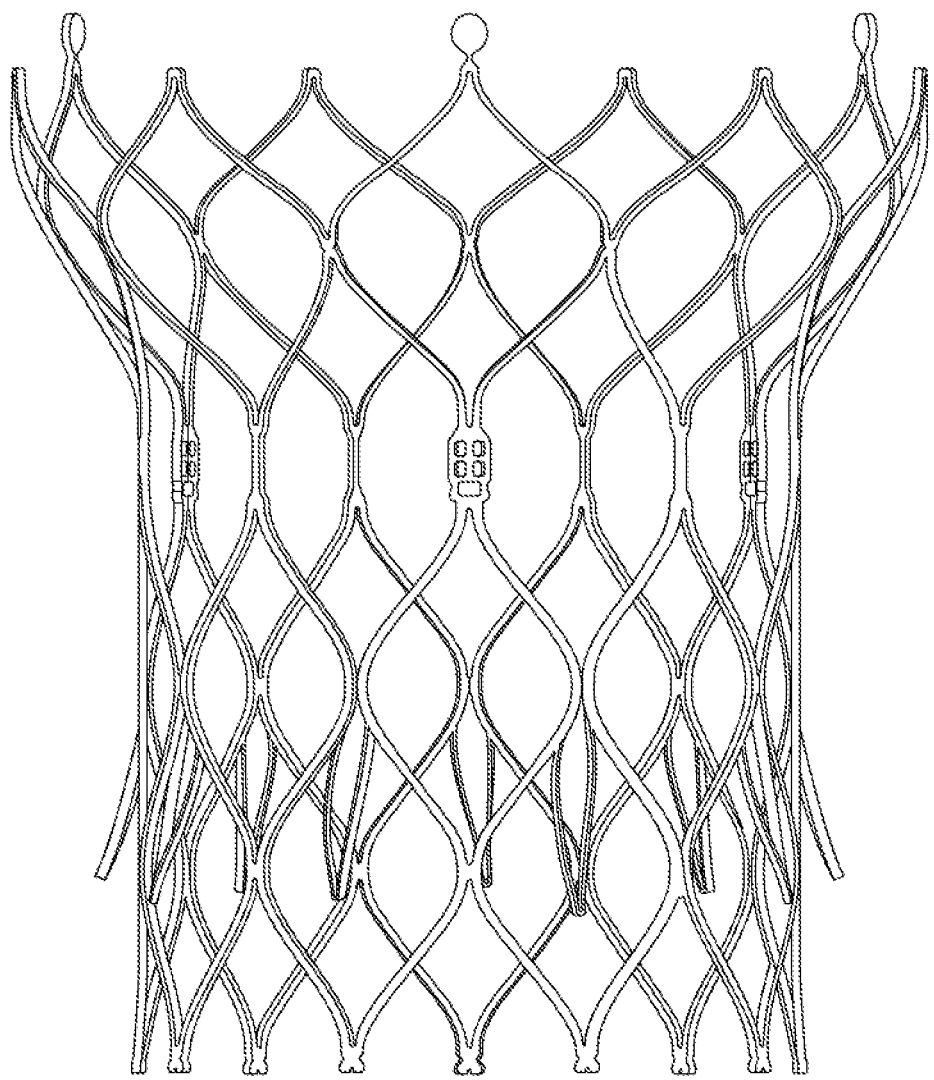
FIG. 10B is a front view of a collapsible prosthetic heart valve in an expanded condition and having the elongated fingers of FIG. 10A.

Although the foregoing describes various embodiments of fingers for coupling the distal edge 458 of cuff 450 to one or more points in a cell 412, other alternatives may be suitable for this purpose. For example, the fingers may be formed with a longer length in the collapsed condition of stent 402 than the fingers described above in connection with FIGS. 5A-7B and those shown in FIGS. 9A-C. Fingers 460' having a length greater than the length of the fingers 460 shown in FIGS. 9A-C are shown in FIGS. 10A-B. Fingers 460' terminate with free ends that are at about the same location in cells 412 as fingers 460 shown in FIGS. 9A-C. That is, as with the fingers 460 of FIG. 9A-C, the free ends of fingers 460' are positioned in the vicinity of ancons 415 which join adjacent cells 412 to one another. The greater length of fingers 460' is accommodated by attaching the fingers at a position closer to the distal apices of cells 412 than are the connections for fingers 460. As a result of the increased length of fingers 460', fingers 460' require a smaller angle of radially outward deflection than fingers 460 in order to have the tips of fingers 460' positioned at the same outward distance from the body of stent 402 as fingers 460' in the expanded condition. This smaller angular deflection results in less strain at the points at which fingers 460' attach to the struts of cell 412. Moreover, as the struts of fingers 460' are attached closer to the apices of cells 412, the struts of the fingers do not spread apart as widely when stent 402 is expanded. This further reduces the strain at the points at which fingers 460' are attached to the cell struts.

In another alternative, one or more sutures may take the place of the fingers. That is, one or more sutures may be attached between a cell 412 and the distal edge 458 of outer cuff 450 in a configuration similar to finger 460 (single suture), similar to finger 460a (one or more sutures forming a "V" shape), or similar to finger 460b (one or more sutures forming a "Y" shape). Further, it should be understood that the various fingers shown in, and described in connection with, FIGS. 5A-J may be partially or entirely replaced by sutures. For example, finger 460j of FIG. 5J may include struts 461j, 463j formed of a shape-memory metal, with the third strut 465j being replaced by a suture coupled to the proximalmost apex of cell 412 or to one of the proximalmost struts of the cell. Using sutures instead of fingers may enable the distal edge 458 of outer cuff 450 to move radially outward from the cell 412 adjacent to where attachment point S2 is located. Although the use of sutures instead of fingers may make it easier to collapse the prosthetic heart valve to a small circumference for loading into a delivery device, it may increase the reliance on pressure from retrograde blood flow around the abluminal surface of stent 402 to billow outer cuff 450 outwardly, since it may not be possible to shape set the sutures to be biased radially outwardly.

Figure 11:
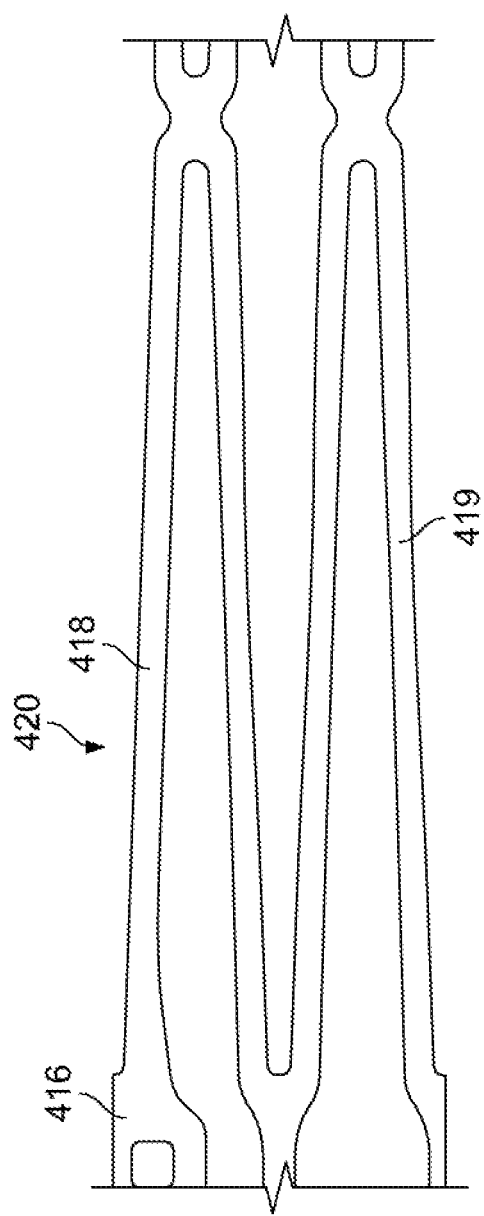
FIG. 11 is an enlarged view of an isolated aortic portion of a stent in a collapsed condition and having tapered strut widths.

In addition to tapering the struts 414 in the annulus section of stent 402, other modifications to the stent to improve its performance are contemplated herein. In that regard, during the percutaneous delivery of the prosthetic heart valve to the implantation site, the heart valve may have to navigate through a tortuous path, including the tight curve of the aortic arch. In order to facilitate the navigation of these pathways, it may be desirable to configure the prosthetic heart valve so that it more easily bends when traversing a tight curve. This may be achieved by tapering the struts in the transition section or aortic section of stent 402, as shown in FIG. 11. Typically, the strut width in the transition and aortic sections of stent 402 will be less than the strut width in the annulus section of the stent since the transition and aortic sections do not have to exert as much radial force as the annulus section exerts to hold the stent in place in the native valve annulus. As shown in FIG. 11, most of the struts in the first row of struts 420 distal to commissure attachment features 416 have been tapered in a region between the ends of the strut. Preferably, the struts may be tapered by an amount sufficient to reduce the width of the struts in the tapered region by about 10% to about 90%, more preferably by about 20% to about 50%. Preferably, not every strut in the first row of struts 420 is tapered. Rather, each of the struts 419 in row of struts 420 may be tapered with the exception of struts 418 that are directly connected to a commissure attachment feature 416. As the attachment of the valve leaflets to commissure attachment features 416 causes a substantial strain to be exerted on the commissure attachment features, and on the struts 418 to which they are attached, during the repeated opening and closing of the valve leaflets, it is preferable that the strength of struts 418 not be diminished by tapering. However, tapering the other struts 419 in the first row 420 causes stent 402 to be somewhat weakened in this region, resulting in a hinge-like effect as stent 402 kinks or bends as it traverses sharp curves in the patient's vasculature.

Figure 12:
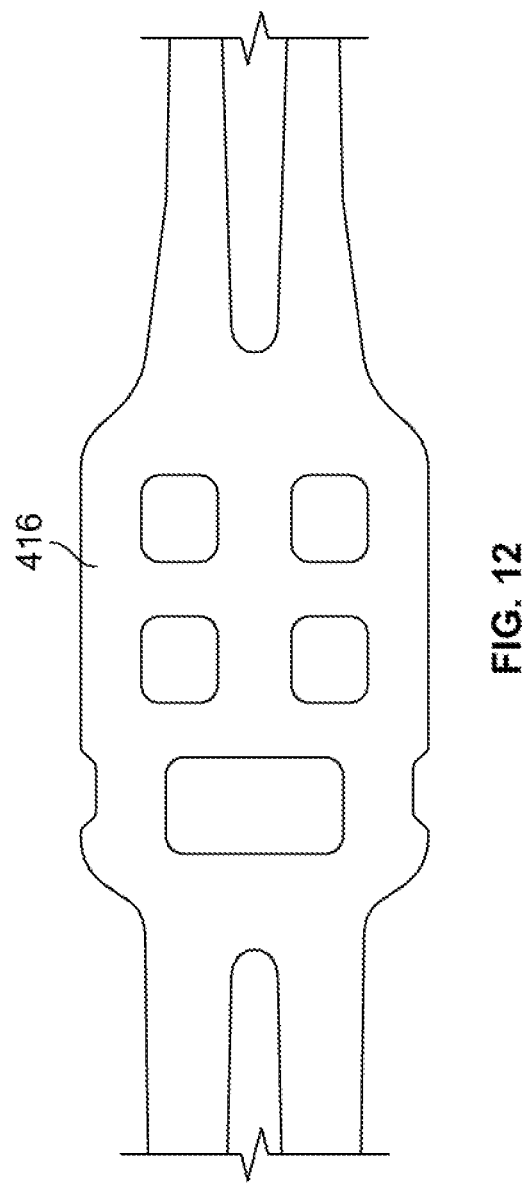
FIG. 12 is an enlarged view of a commissure attachment feature having reinforced connections to the remainder of the stent.

Yet a further modification to stent 402 is illustrated in FIG. 12. It is generally known that the highest strain experienced by stent 402 is at the commissure attachment features 416, and in particular, at the junction of the commissure attachment features with the struts forming the cells 412 immediately proximal to and distal to the commissure attachment features. In order to reinforce this junction, the ends of the cell struts connected to commissure attachment features 416 may be widened so as to make the transition therebetween more gradual. To ease the transition between the commissure attachment features 416 and the struts forming the cells 412 in the annulus section of stent 402 immediately proximal to the commissure attachment features, the width of these struts may be gradually increased by between about 5% and about 70%, preferably by between about 10% and about 20%. The struts forming the cells 412 in the transition and aortic sections of stent 402 may be similarly widened. To ease the transition between commissure attachment features 416 and the struts forming the cells 412 in the transition and/or aortic sections of stent 402 immediately distal to the commissure attachment features, the width of these struts may be gradually increased by between about 5% and about 90%, preferably by between about 30% and about 80%.

Figure 13A:
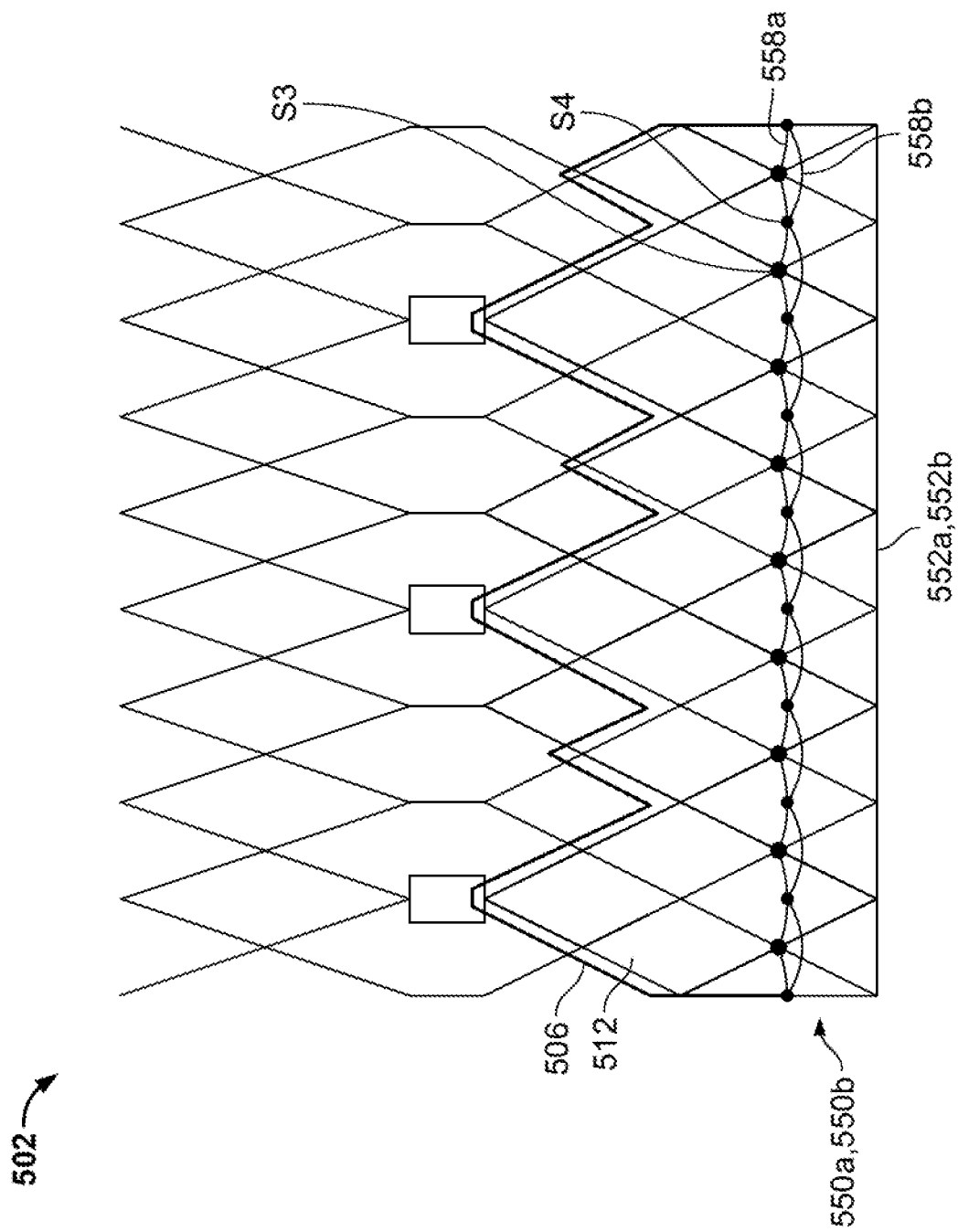
FIG. 13A is a schematic developed view of a stent in an expanded condition with two outer cuffs according to another embodiment of the disclosure.

The problem solved by the fingers described above may be solved with additional or alternative features, such as the use of two outer cuffs. For example, FIG. 13A illustrates a stent 502 and a first outer cuff 550a that are identical to the stent 302 and outer cuff 350 of FIG. 3A. With the exception of a second outer cuff 550b described below, a prosthetic heart valve incorporating stent 502 may be identical to the prosthetic heart valve incorporating stent 302 described above. As with outer cuff 350, the proximal edge 552a of first outer cuff 550a may be attached to stent 502 and/or to an inner cuff 506 at or near the inflow end of the stent. Also, the distal edge 558a of first outer cuff 550a may be coupled to stent 502 and/or to inner cuff 506 at first attachment points S3 that are spaced apart along the circumference of the stent. For example, the distal edge 558a of first outer cuff 550a may be attached to stent 502 at points at which adjacent cells 512 in the proximalmost row of full cells meet one another. A second outer cuff 550b may be similar or nearly identical in construction to first outer cuff 550a, although second outer cuff 550b may have a slightly greater length in the circumferential direction (or a greater circumference if formed in a tubular shape) compared to first outer cuff 550a. Second outer cuff 550b may be positioned radially outward of first outer cuff 550a in a stacked fashion. Second outer cuff 550b may also have a proximal edge 552b attached to stent 502 and/or to inner cuff 506 at or near the inflow end of the stent. Preferably, a single suture is used to couple the proximal edge 552a of first outer cuff 550a and the proximal edge 552b of second outer cuff 550b to stent 502 and/or to inner cuff 506 so as to limit the bulk of the assembly. However, the distal edge 558b of second outer cuff 550b is not attached directly to stent 502. Rather, the distal edge 558b of second outer cuff 550b is attached to the distal edge 550a of first outer cuff 550a at attachment points S4 spaced around the circumference of stent 502. Preferably, attachment points S4 are positioned at the midpoint between each pair of adjacent attachment points S3.

Figure 13B:
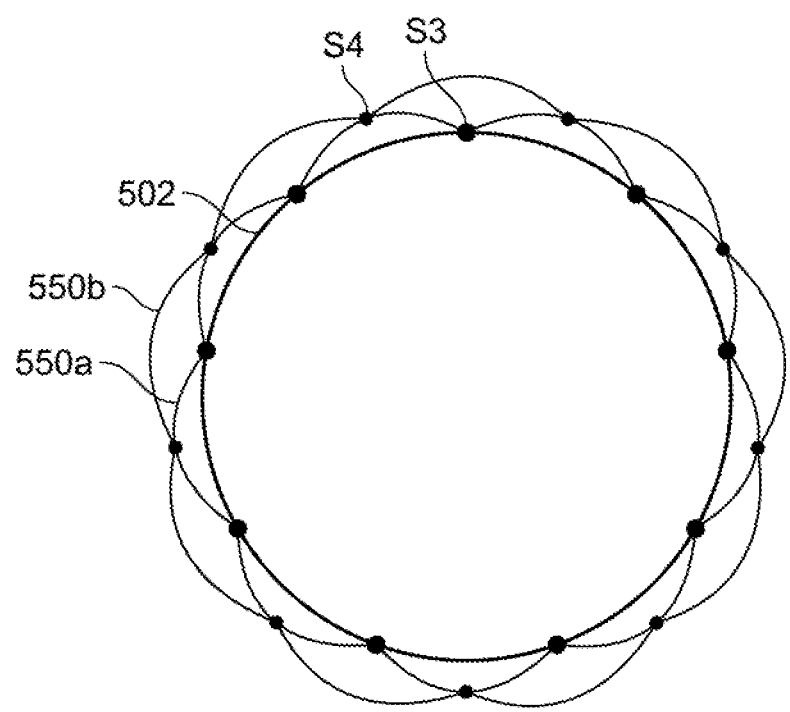
FIG. 13B is an end view of the stent and outer cuffs of FIG. 13A looking from the outflow end of the stent.
Figure 13C:
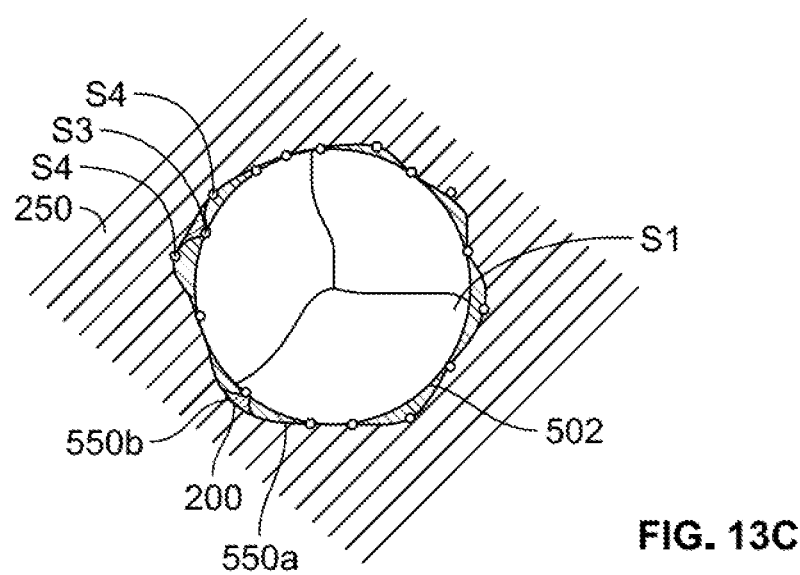
FIG. 13C is a highly schematic transverse cross-sectional view of a prosthetic heart valve including the stent and cuffs of FIG. 13A implanted in a patient.

In the configuration described directly above, the attachment of second outer cuff 550b to first outer cuff 550a should not inhibit the first outer cuff from billowing outwardly as retrograde blood flow along the abluminal surface of stent 502 enters the space between inner cuff 506 and the first outer cuff. The same retrograde blood flow may also cause second outer cuff 550b to billow outwardly with respect to first outer cuff 550a. Although first outer cuff 550a may be prevented from billowing outwardly from inner cuff 506 at attachment points S3, since attachment points S4 are circumferentially staggered with respect to attachment points S3, second outer cuff 550b will be able to billow outwardly from the first outer cuff and from inner cuff 506 at points that are radially aligned with attachment points S3. This point may be better understood from the top view of stent 502 having first and second outer cuffs 550a, 550b, as shown in FIG. 13B, as well as from the cross-sectional view of a valve including stent 502 and outer cuffs 550a, 550b implanted in a native annulus, as shown in FIG. 13C. A comparison of FIGS. 3B and 13C shows that retrograde blood flow that could otherwise leak around first outer cuff 550a at attachment points S3 may instead be captured between first outer cuff 550a and second outer cuff 550b.

With the configuration described above, at least one pocket may be formed between inner cuff 506 and first outer cuff 550a, with a plurality of openings leading into the at least one pocket, the openings being positioned between adjacent attachment points S3. Similarly, at least one pocket may be formed between first outer cuff 550a and second outer cuff 550b, with a plurality of openings leading into the at least one pocket, the openings being positioned between adjacent attachment points S4.

Figure 14:
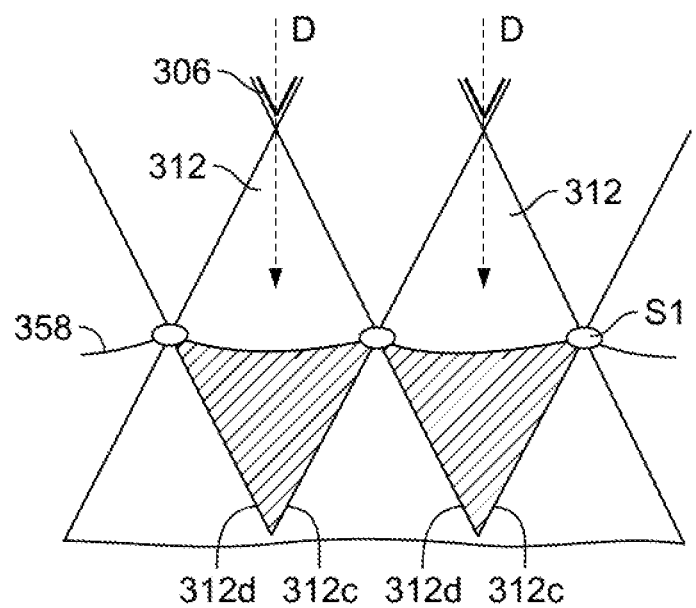
FIG. 14 is a highly schematic view of retrograde blood flowing into a portion of the outer cuff on the stent of FIG. 4A.

Another potential issue that may arise with the outer cuff 350 of FIG. 3A is that, after retrograde blood flow passes the distal edge 358 of the outer cuff and enters the space between the outer cuff and inner cuff 306, blood may not easily be able to migrate past the cell struts located between the inner and outer cuffs toward the proximal edges of the cuffs. To illustrate this point, an enlarged view of the inflow end of stent 302, outer cuff 350 and inner cuff 306 is shown in FIG. 14. As blood flows in the retrograde direction D around the abluminal surface of stent 302, the blood can enter the space between outer cuff 350 and inner cuff 306 via the openings between attachment points S1, as described above. However, if outer cuff 350 is taut when stent 302 is in the expanded condition, blood may not be able to pass across struts 312c and 312d into the space of adjacent cells (or half-cells), such as those directly under attachment points S1. This restriction may keep those areas of outer cuff 350 from billowing outwardly to fill any gaps 200 between native valve annulus 250 and the implanted prosthetic valve. This particular restriction may be mitigated by using the fingers described in connection with FIGS. 4A-5F to push the distal edge 358 of outer cuff 350 radially outward and away from struts 312c and 312d, or may be avoided by using the second outer cuff 550b described in connection with FIGS. 13A-C. However, other techniques, such as providing pleats in outer cuff 350, may also help reduce this potential problem, as described in greater detail below.

Figure 15A:
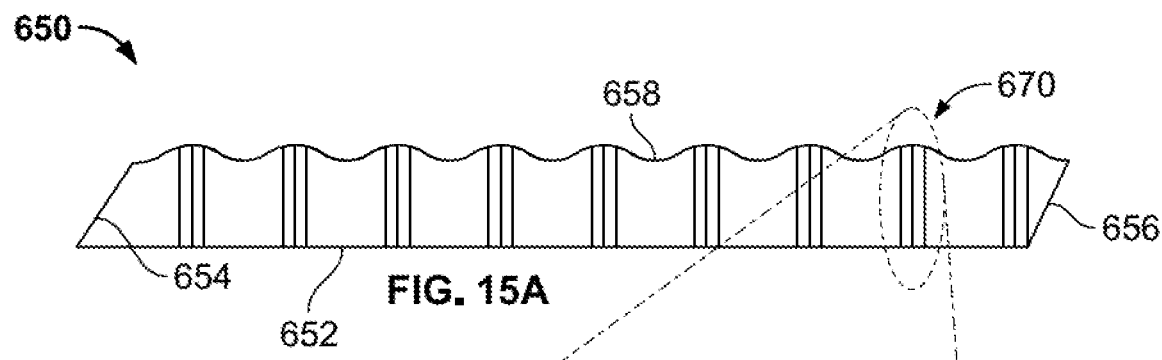
FIG. 15A is a highly schematic partial side view of an outer cuff with pleats extending in an axial direction of the heart valve according to another embodiment of the disclosure, the pleats being shown in a flattened condition.

FIG. 15A illustrates a pleated outer cuff 650 that may be used instead of cuff 350 with a stent similar or identical to stent 302. Outer cuff 650 generally has a straight inflow or proximal edge 652, correspondingly angled side edges 654 and 656, and a scalloped outflow or distal edge 658, and may be formed from any of the materials noted above for forming the other cuffs described herein, either from a single piece of material, from more than one piece of material, or as a single tubular member. As shown, outer cuff 650 may be wrapped around stent 302 and edges 654 and 656 may be sewn or otherwise attached to one another. The proximal edge 652 of outer cuff 650 may be attached to the inflow end of stent 302 and/or to an inner cuff (not shown in FIGS. 15A-C) similar or identical to inner cuff 306, at any height along the cuff, for example by a continuous line of sutures. Although other cuffs herein are shown with a straight distal edge, it should be noted that those cuffs may have a scalloped distal edge as shown in FIG. 15A. Similarly, outer cuff 650 may have a substantially straight distal edge 658, rather than a scalloped edge. Preferably, the attachment points coupling the distal edge 658 of outer cuff 650 to stent 302 are positioned at the peaks of the distal edge, with the troughs not being directly coupled to the stent.

Figure 15B:
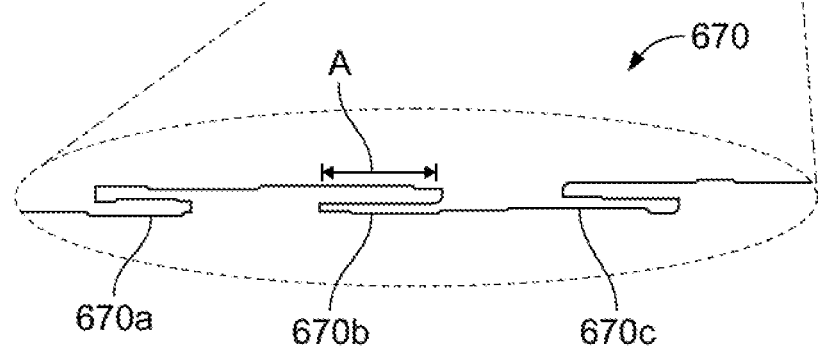
FIG. 15B is an enlarged end view of a group of the axial pleats of FIG. 15A.
Figure 15C:
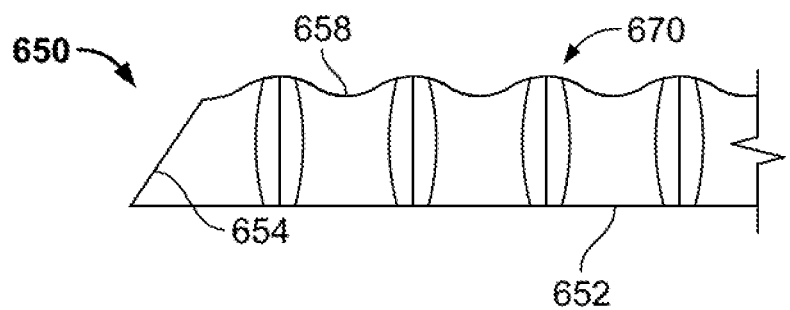
FIG. 15C is a highly schematic partial side view of the outer cuff of FIG. 15A, showing the pleats in a billowed out condition.

Outer cuff 650 may include a plurality of groups of pleats 670. In the illustrated embodiment, outer cuff 650 includes nine groups of pleats 670 extending in the axial direction, with each group of pleats 670 being circumferentially aligned with a peak of distal edge 658. FIG. 15B illustrates an end view of one of the groups of pleats 670 shown in FIG. 15A. Each group of pleats 670 may include one, two, or more pleats. In the illustrated embodiment, each group of pleats 670 includes three pleats 670a-c, each such pleat having a double fold so as to create an area of overlap A. With the presence of axial pleats 670, the actual length of outer cuff 650 between side edges 654 and 656, when the pleats are expanded, is greater than the circumference of stent 302 in the expanded condition. In particular, for pleats 670a-c having double folds, the extended length of outer cuff 650 may be increased by a factor of approximately twice the length of the overlap A for each individual pleat in the groups of pleats 670. Although each pleat 670a-c may be coupled to stent 302 and/or to inner cuff 306 at the proximal edge 652 and the distal edge 658 of outer cuff 650, there preferably are no sutures coupling the folds of pleats 670a-c to one another between the proximal and distal edges of the outer cuff. With this configuration, as blood enters the space between outer cuff 650 and inner cuff 306, for example at the troughs in distal edge 658 between the attachment points S1 to stent 302, pleats 670a-c provide slack so that the blood may pass across struts 312c and 312d, causing pleats 670a-c to billow outwardly, as shown in FIG. 15C. The outward billowing of pleats 670a-c would be in addition to the outward billowing of outer cuff 650 that would be similar to the outward billowing described in connection with outer cuff 350. It should be noted that each group of pleats 670 does not have to be circumferentially aligned with a peak of distal edge 658, but preferably at least some area of overlap A of a pleat is positioned in radial alignment with the struts 312c and/or 312d of each cell 312 to help ensure enough slack for blood to cross those struts. In addition to allowing for blood to migrate within the spaces between outer cuff 650 and inner cuff 306, the additional material provided by the groups of pleats 670 may also allow for a greater amount of outward billowing as a result of retrograde blood flow, which may, in turn, help better seal the native valve annulus and mitigate PV leak.

Pleats 670a-c may be created by manually or otherwise folding outer cuff 650 back and forth on itself, and then applying heat and/or force, such as by a heated iron or a similar device, to set the shape of the pleats. With this configuration, the groups of pleats 670 retain their shape prior to implantation, allowing outer cuff 650 to remain taut over stent 302, which may reduce the forces encountered upon loading the prosthetic valve into a delivery device in a collapsed condition. It may be preferable to store such a prosthetic valve in a dry state to help the groups of pleats 670 retain their shape prior to implantation.

In FIG. 15A, one group of pleats 670 is shown at each peak, with each group of pleats 670 corresponding to one of the nine cells 312 in the proximalmost row of cells in stent 302. However, this one-to-one correspondence is not necessary. For example, more or fewer groups of axial pleats 670 may be provided than shown, and each group of pleats may include folds having more or less overlapping length A than shown. In addition, although pleats 670a-c are shown with double folds, other folds, such as quadruple folds, may be used. Thus, the present disclosure contemplates an outer cuff 650 having a single pleat with two or more folds, a group of pleats with each pleat having two or more folds, or multiple groups of such pleats.

Instead of having groups of axial pleats 670, an outer cuff 750 may include at least one group of pleats 770 extending in the circumferential direction, as shown in FIGS. 16A-C. Outer cuff 750 may be used with a stent similar or identical to stent 302 and an inner cuff similar or identical to inner cuff 306. Outer cuff 750 may be formed from the same materials and may have the same general shape, other than the pleats, as outer cuff 650, including a straight inflow or proximal edge 752, angled side edges 754 and 756, and a scalloped outflow or distal edge 758. Outer cuff 750 may be wrapped around stent 302 and edges 754 and 756 may be sewn or otherwise attached to one another. The proximal edge 752 of outer cuff 750 may be sutured in a substantially continuous manner to the inflow end of stent 302 and/or to inner cuff 306 at any location along its height, and the attachment points coupling the distal edge 758 of the outer cuff to the stent are preferably positioned at the peaks of the distal edge, with the troughs not being directly coupled to the stent.

Outer cuff 750 may include one or more groups of pleats 770. In the illustrated embodiment, outer cuff 750 includes one group of circumferential pleats 770, with the individual pleats extending mostly or entirely along the circumference of outer cuff 750 from one side edge 754 to the other side edge 756. FIG. 16B illustrates a cross-sectional view of the group of pleats 770 taken transverse to the length direction of the pleats. The group of pleats 770 may include one, two, or more pleats. In the illustrated embodiment, the group of pleats 770 includes three pleats 770a-c, each pleat having a double fold so as to create an area of overlap A. However, rather than increasing the length of outer cuff 750 between side edges 754 and 756, as is the case with outer cuff 650, the group of circumferential pleats 770 increases the extent of outer cuff 750 in the axial direction of the heart valve between proximal edge 752 and distal edge 758 when the pleats are expanded. In particular, for pleats 770a-c having double folds, the axial extent of outer cuff 750 may be increased by a factor of approximately twice the extent of the overlap A for each individual pleat in the group of pleats 770. There preferably are no sutures coupling the folds of pleats 770a-c to one another, with the possible exception that sutures attaching side edge 754 to side edge 756 may at the same time join pleats 770a-c to one another where the side edges meet. With this configuration, as blood enters the space between outer cuff 750 and inner cuff 306, for example at the troughs in distal edge 758 between the attachment points to stent 302, pleats 770a-c provide additional material so that the blood may pass across struts 312c and 312d, enabling the full extent of outer cuff 750 to billow outwardly, as shown in FIG. 16C.

Although outer cuffs with axial pleats or circumferential pleats are described above, other types of pleats that provide for additional space between the outer cuff and the inner cuff are possible. For example, rather than being substantially axial or substantially circumferential, pleats could be folded so they extend at an oblique angle to both the axial and the circumferential directions. For example, if circumferential pleats are thought of as being at an angle of approximately 0 degrees relative to the circumferential direction and axial pleats are thought of as being at an angle of approximately 90 degrees relative to the circumferential direction, pleats having an angle of about 45 degrees or other intermediate angles between 0 degrees and 180 degrees relative to the circumferential direction may be used. In one example, the pleats may be angled so they are substantially aligned with struts 312c or struts 312d of stent 302 (FIG. 14). Providing pleats at angles that correspond to the angles of these struts may facilitate the connection of the outer cuff to stent 302.

In another alternative, both axial pleats and circumferential pleats may be used in a single cuff. For example, groups of axial pleats 670 may first be formed in an outer cuff, with a group of circumferential pleats 770 formed next. Alternately, circumferential pleats 770 may first be created in an outer cuff with axial pleats 670 formed next. The combination of axial and circumferential pleats may allow the outer cuff to billow out to a greater degree than a cuff having only axial or only circumferential pleats. It should also be understood that any of the pleated cuffs described herein may be used in combination with a stent having any of the fingers described herein.

FIGS. 17A-D illustrate various embodiments of a prosthetic heart valve that incorporate a stent 802 that may be the same as or similar to stents 102 and 302 described above. Stent 802 may be used in a prosthetic heart valve that is similar or identical to prosthetic heart valve 100 described above, with certain exceptions. The annulus section 840 of stent 802 may include two rows of cells 812, similar or identical to those of stent 102, instead of the three rows of stent 302. It should be understood that, in some embodiments, stent 802 may include three or more rows of cells 812 in annulus section 840. Although commissure attachment features 816 of stent 802 are illustrated as open rectangles in FIGS. 17A-D, the commissure attachment features may have a form that is the same as or similar to commissure attachment features 116 shown in FIG. 1, or any other suitable form having any number of rows or columns of eyelets and/or eyelets of different sizes and/or shapes positioned in any arrangement on the commissure attachment feature. Stent 802 may also include struts having a tapered width as described in connection with other stents herein, whether or not the stent 802 includes fingers similar or identical to those described above. An inner cuff 806 similar or identical to cuff 106 may be positioned on the luminal and/or abluminal side of stent 802. Rather than a scalloped inflow end as with cuff 106, however, cuff 806 may have a straight inflow end. FIGS. 17A-D illustrate various outer cuffs 850a-d that may be connected to stent 802 and/or to cuff 806. Outer cuffs 850a-d may be generally the same as outer cuff 350 described in connection with FIG. 3A, with certain exceptions. For example, cuffs 850a-d may be wrapped around the circumference of stent 802 at the inflow end of the stent so as to overlap in the longitudinal direction of the stent with cuff 806. It should be understood that, in FIGS. 17A-18D, the portions of cells 812 covered by outer cuffs 850a-d are illustrated in dashed lines. Outer cuffs 850a-d may each be a single piece of material having similar substantially straight proximal edges 852a-d and side edges 854a-d, 856a-d, although in other embodiments the outer cuffs may be formed of multiple pieces of material coupled to one another. However, the distal edges 858a-d of outer cuffs 850a-d may have structures that are different from one another and different from the distal edge 358 of outer cuff 350. Preferably, the proximal edges 852a-d of the respective outer cuffs 850a-d are coupled to stent 802 and/or to inner cuff 806 at or near the inflow end of the stent, for example by a continuous line of sutures (not shown), with the side edges 854a-d and 856a-d of the respective outer cuffs joined to one another so that retrograde blood flow entering the space between the outer cuff and the inner cuff cannot pass in the retrograde direction beyond the combined cuffs. The distal edges 858a-d of the respective outer cuffs 850a-d may have a structure that allows retrograde blood flow to enter the space between the outer cuff and inner cuff 806. Although the direct attachment of the straight distal edge 358 of outer cuff 350 to stent 302 and/or to inner cuff 306 at attachment points S1 may result in certain drawbacks described above, the various alternative distal edges 858a-d of outer cuffs 850a-d may reduce or eliminate such drawbacks.

Figure 17A:
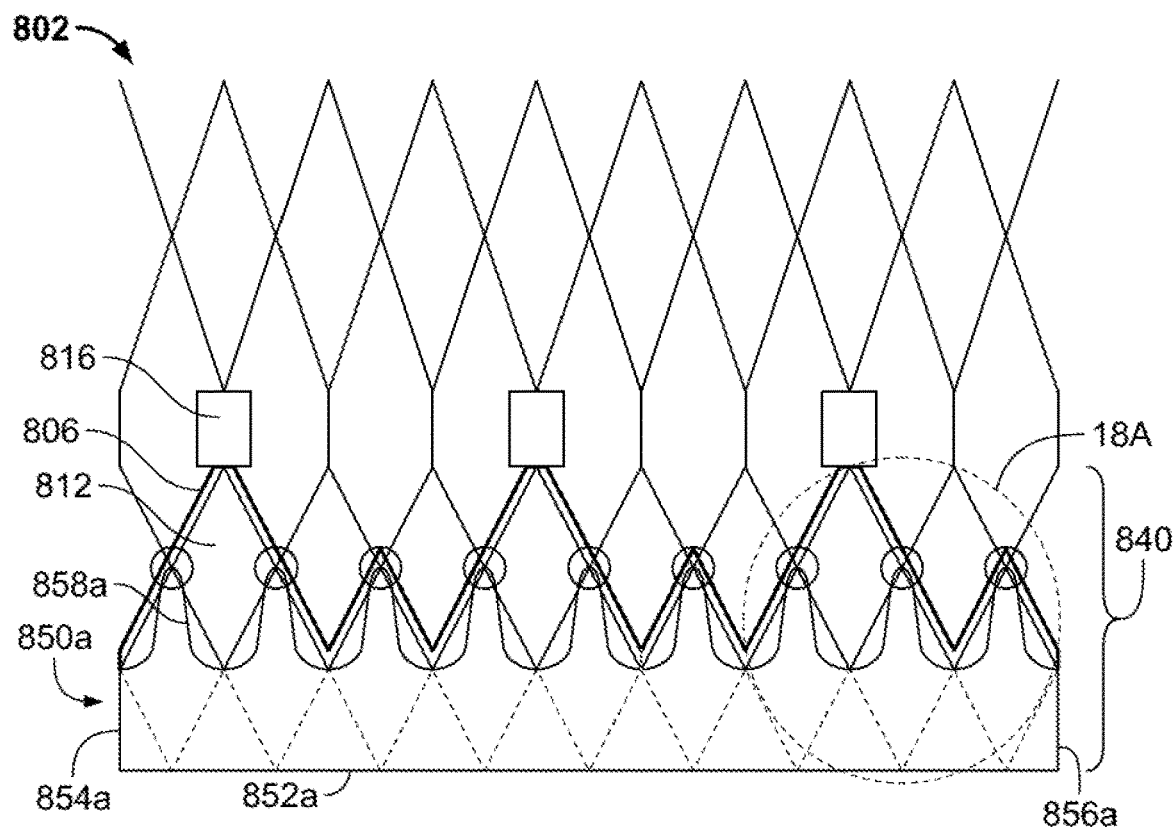
FIGS. 17A-D are schematic developed views of a stent with an outer cuff in an expanded condition according to additional embodiments of the disclosure.
Figure 18A:
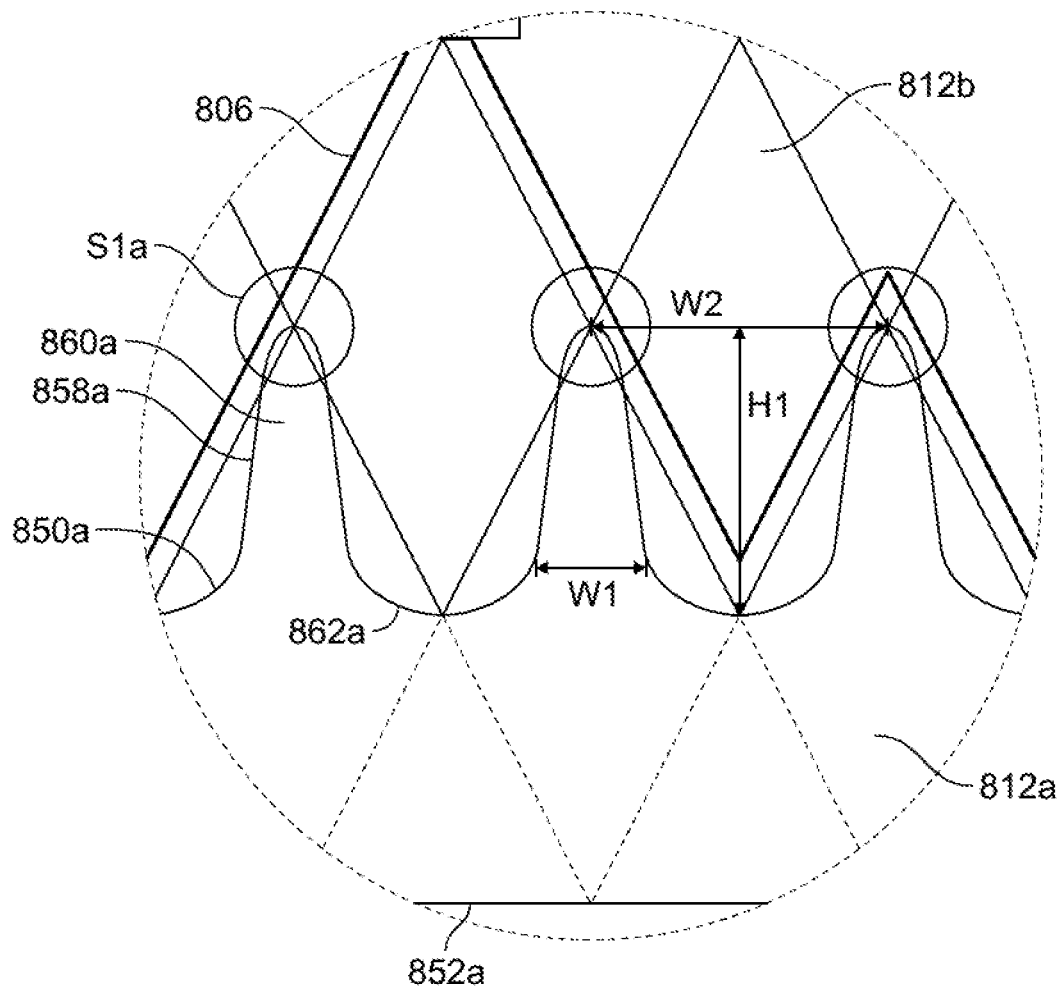
FIGS. 18A-D are enlarged partial views of the portions of FIGS. 17A-D respectively labeled as 18A-D.

Referring to FIGS. 17A and 18A, the distal edge 858a of outer cuff 850a may be attached to stent 802 and/or to inner cuff 806 at locations that are spaced apart in the circumferential direction. The distal edge 858a of outer cuff 850a may, for example, be sutured to inner cuff 806 and/or to stent 802 at attachment points S1*a* located where each cell 812*b* in the second circumferential row of cells intersects with an adjacent cell in that same row. Distal edge 858*a* may be scalloped to form a plurality of rounded peaks 860*a*, with each peak being attached to inner cuff 806 and/or to stent 802 at an attachment point S1*a*. Each pair of adjacent peaks 860*a* of the distal edge 858*a* of outer cuff 850*a* may be connected by a rounded trough 862*a*, with the proximalmost portion of the rounded trough substantially aligning with the intersection between one cell 812*a* in the first or proximalmost row of cells and an adjacent cell in that same row. Preferably, the peaks 860*a* of outer cuff 850*a* are narrower in width in the circumferential direction than the troughs 862*a* so that struts that are common to cells 812*a* and 812*b* are at least partially uncovered by outer cuff 850*a*. With this configuration, the distal edge 858*a* of outer cuff 850*a* may present a relatively large length that is not directly attached to stent 802 and/or to inner cuff 806 so that retrograde blood flow around the outside of the stent may readily enter the space between the outer cuff and the inner cuff to help mitigate PV leak.

In the illustrated example of outer cuff 850*a* in FIG. 18A, the widest portion of each peak 860*a* in the circumferential direction is located at the base of the peak. In other words, the base of a peak 860*a* is located where the peak transitions into troughs 862*a* on either side of the peak, and the base of the peak may have a width W1 in the circumferential direction of stent 802. Width W1 is preferably smaller than the width W2 of cells 812*b* in the circumferential direction of stent 802 when the stent is in the expanded condition. In the illustrated embodiment, width W2 is also approximately equal to the width in the circumferential direction between the distalmost points of two adjacent peaks 860*a*. Still further, in the illustrated embodiment, each peak 860*a* may have a height H1 measured in the longitudinal direction of the stent between the proximalmost point of a trough 850*a* and the distalmost point of an adjacent peak. The height H1 of each peak 860*a* may be substantially equal to the width between the distalmost points of two adjacent peaks. Although these relative dimensions are intended to be exemplary in nature, the relatively narrow peaks 860*a* combined with the relatively wide troughs 862*a*, as well as the relatively large distance between the tops of adjacent peaks, may help to present a large unattached area of the distal edge 858*a* of outer cuff 850*a* to increase the likelihood of capturing retrograde blood flow around the outside of stent 802.

Figure 17B:
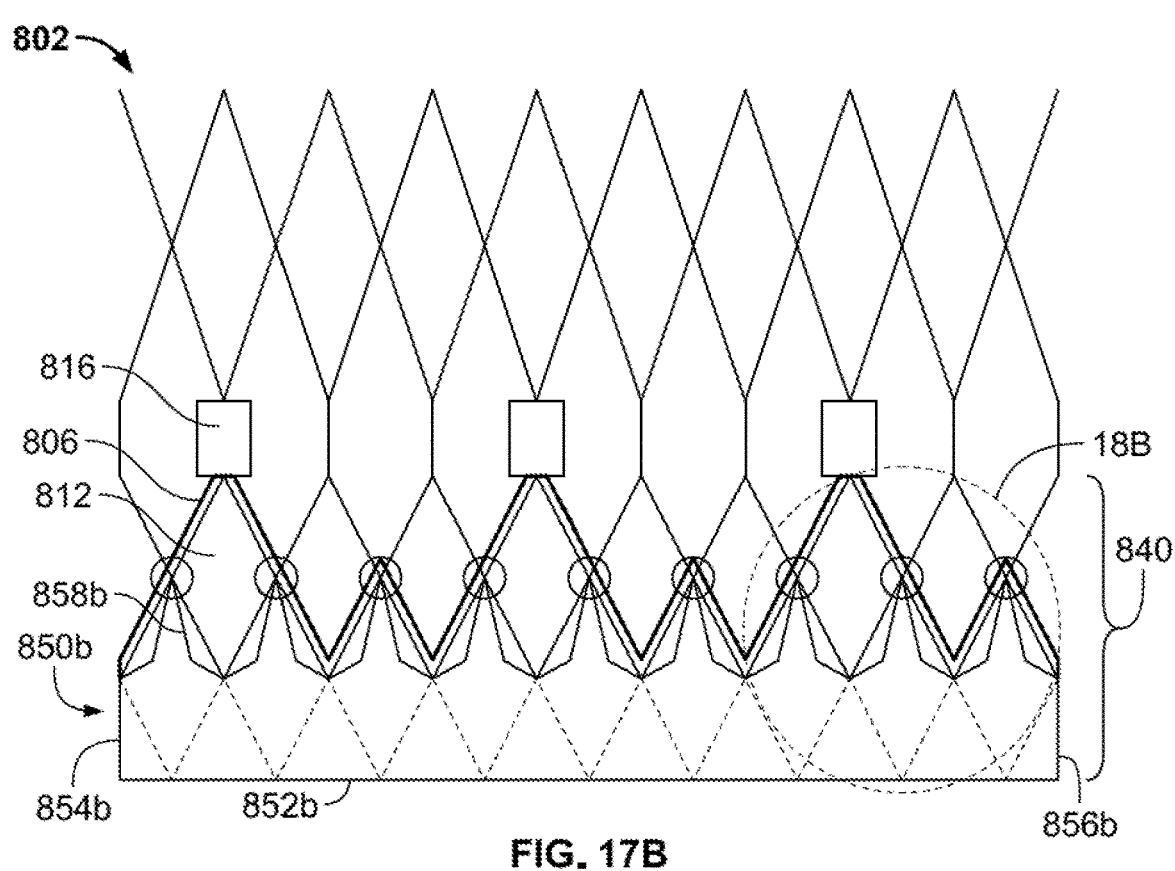
Figure 18B:
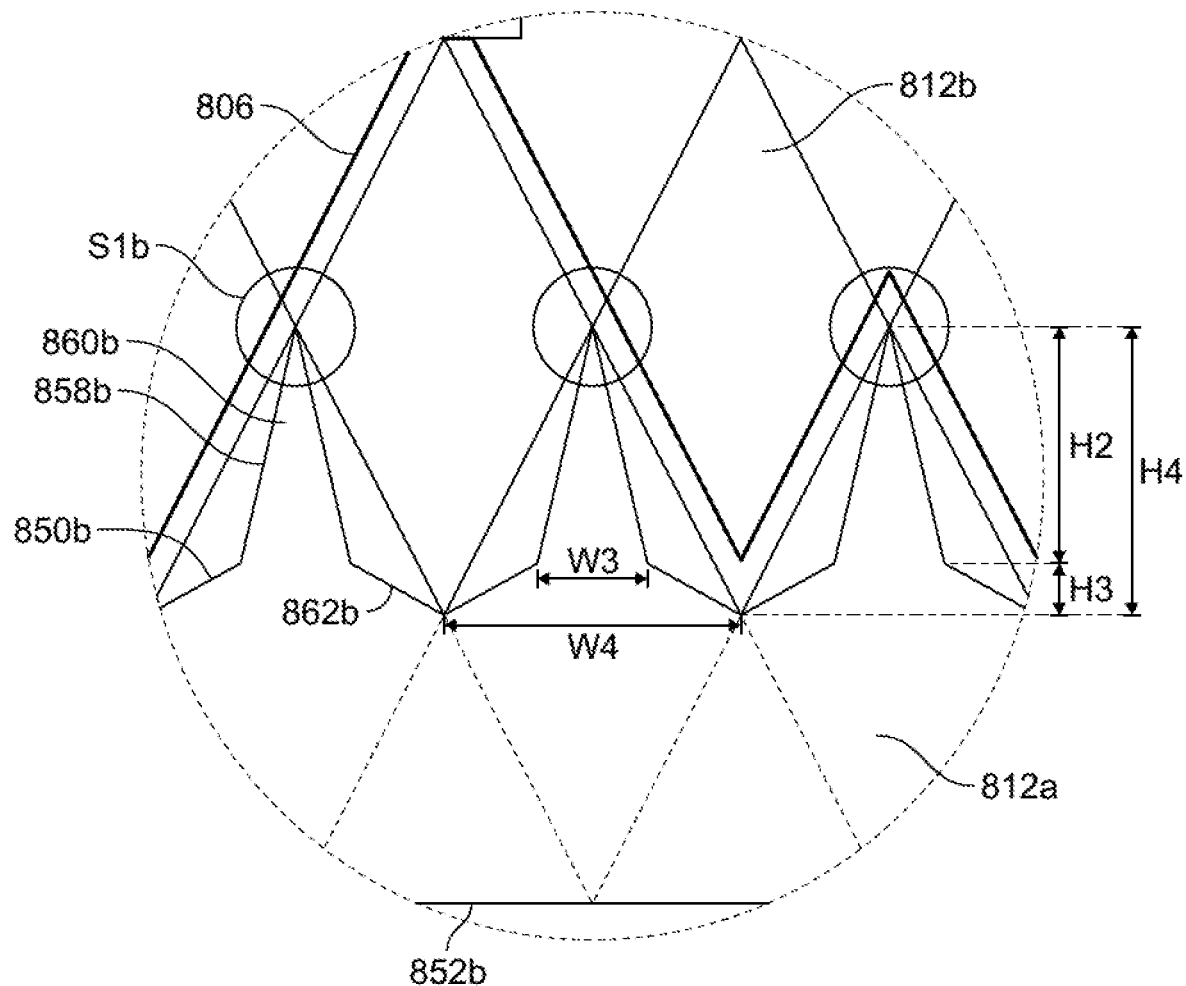

Referring to FIGS. 17B and 18B, the distal edge 858*b* of outer cuff 850*b* may be attached to stent 802 and/or to inner cuff 806 at locations that are spaced apart in the circumferential direction. Similar to outer cuff 850*a*, the distal edge 858*b* of outer cuff 850*b* may, for example, be sutured to inner cuff 806 and/or to stent 802 at attachment points S1*b* located where each cell 812*b* in the second circumferential row of cells intersects with an adjacent cell in that same row. Distal edge 858*b* may include a plurality of peaks 860*b* with substantially straight edges, with each peak being attached to inner cuff 806 and/or to stent 802 at an attachment point S1*b*. In the illustrated embodiment, each peak 860*b* may have a pointed distalmost end attached at an attachment point S1*b*, with the peak being substantially triangular with the distalmost portion of the peak forming an acute angle. Each peak 860*b* may gradually increase in width for a height H2 in the longitudinal direction toward the proximal or inflow end of stent 802. The portions of the distal edge 858*b* of outer cuff 850*b* connecting two adjacent peaks 860*b* may form a trough 862*b*, with the trough having substantially straight edges. The portions of distal edge 858*b* forming a trough 862*b* may extend a height H3 in the longitudinal direction of the stent 802, with height H3 preferably being smaller than height H2. The combined height H4 of a trough 862*b* and a peak 860*b* being the sum of heights H2 and H3.

Still referring to FIG. 18B, the proximalmost portion of each peak 860*b* may extend a width W3 in the circumferential direction of stent 802. The proximalmost portions of adjacent troughs 862*b* may be spaced apart a width W4 in the circumferential direction of the stent 802, which may be about equal to the maximum width of a cell 812*a* in the expanded condition of the stent. Width W3 is smaller than width W4. Preferably, width W3 is between about one half and about one fifth width W4. Further, width W4 may be about equal to height H4. With the illustrated configuration, struts that are common to cells 812*a* and 812*b* are at least partially uncovered by outer cuff 850*b*, and the distal edge 858*b* of the outer cuff presents a relatively large length that is not directly attached to stent 802 and/or to inner cuff 806 so that retrograde blood flow around the outside of the stent may readily enter the space between the outer cuff and the inner cuff to help mitigate PV leak. Still further, the use of substantially straight edges to form peaks 860*b* and troughs 862*b* may help reduce the tendency of the distal edge 858*b* of cuff 850*b* to roll up on itself during loading, delivery, and/or operation of the heart valve incorporating stent 802 and outer cuff 850*b*.

Figure 17C:
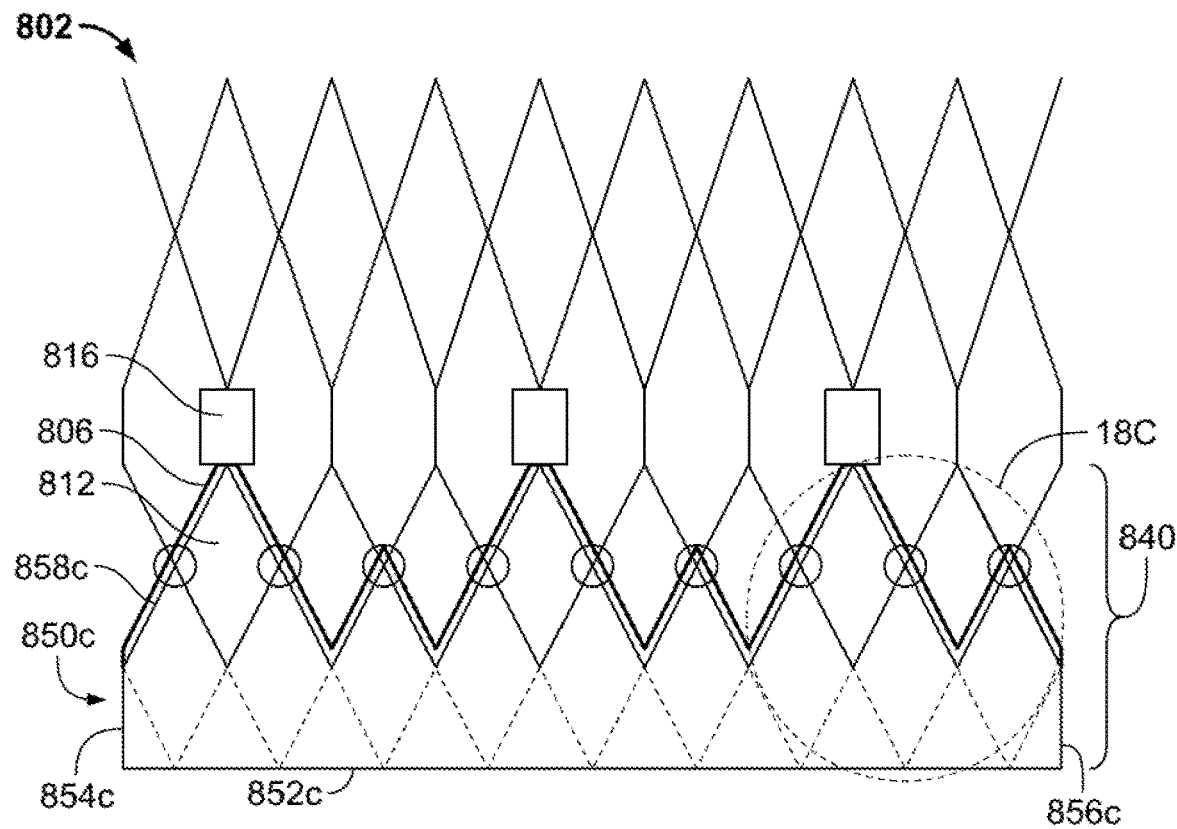
Figure 18C:
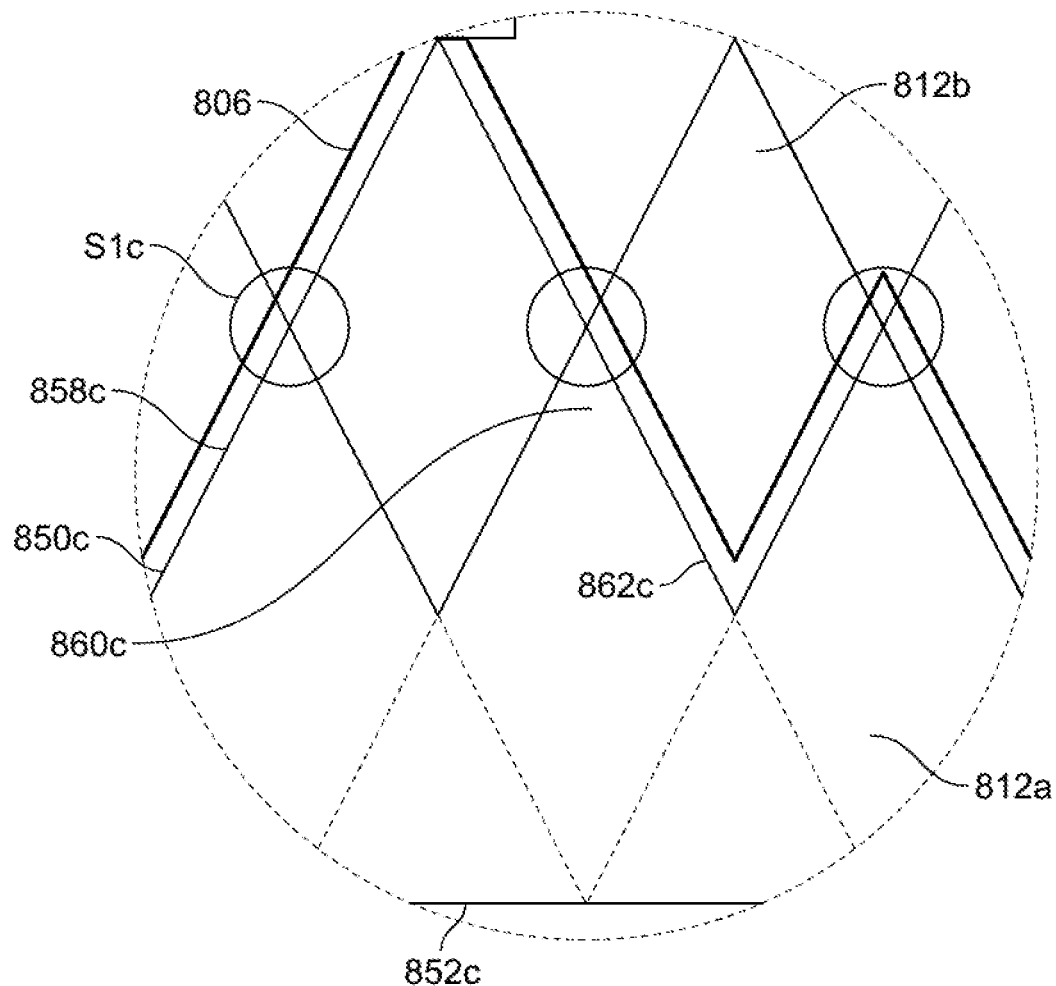

Referring to FIGS. 17C and 18C, the distal edge 858*c* of outer cuff 850*c* may be attached to stent 802 and/or to inner cuff 806 at locations that are spaced apart in the circumferential direction. Similar to outer cuffs 850*a*-*b*, the distal edge 858*c* of outer cuff 850*c* may, for example, be sutured to inner cuff 806 and/or to stent 802 at attachment points S1*c* located where each cell 812*b* in the second circumferential row of cells intersects with an adjacent cell in that same row. Distal edge 858*c* may include a plurality of repeating "V"-shapes, such that the distal edge substantially follows the struts that are common to the cells 812*a* in the first circumferential row of cells and the cells 812*b* in the second circumferential row of cells. In other words, distal edge 858*c* may include a plurality of peaks 860*c* that are substantially aligned with and follow the distal apex of each cell 812*a*, with each pair of adjacent peaks being connected by a trough 862*c* that substantially aligns with or follows the proximal apex of each cell 812*b*. It should be understood that, although the distal edge 858*c* of outer cuff 850*c* may follow the struts common to cells 812*a* and 812*b*, it is preferable that the distal edge is only attached to stent 802 and/or to inner cuff 806 at attachment points S1*c*, leaving a relatively large length of the distal edge unattached so that retrograde blood flow around the outside of the stent may readily enter the space between the outer cuff and the inner cuff to help mitigate PV leak.

Figure 17D:
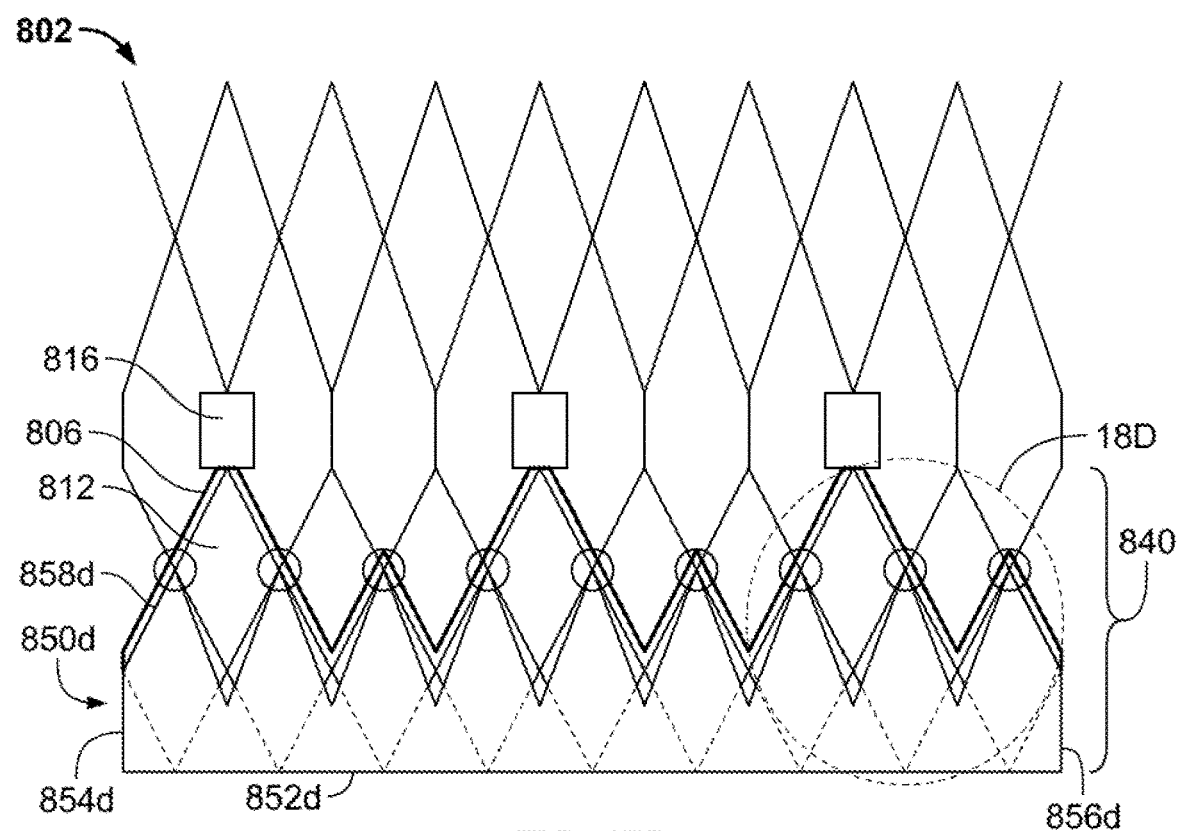
Figure 18D:
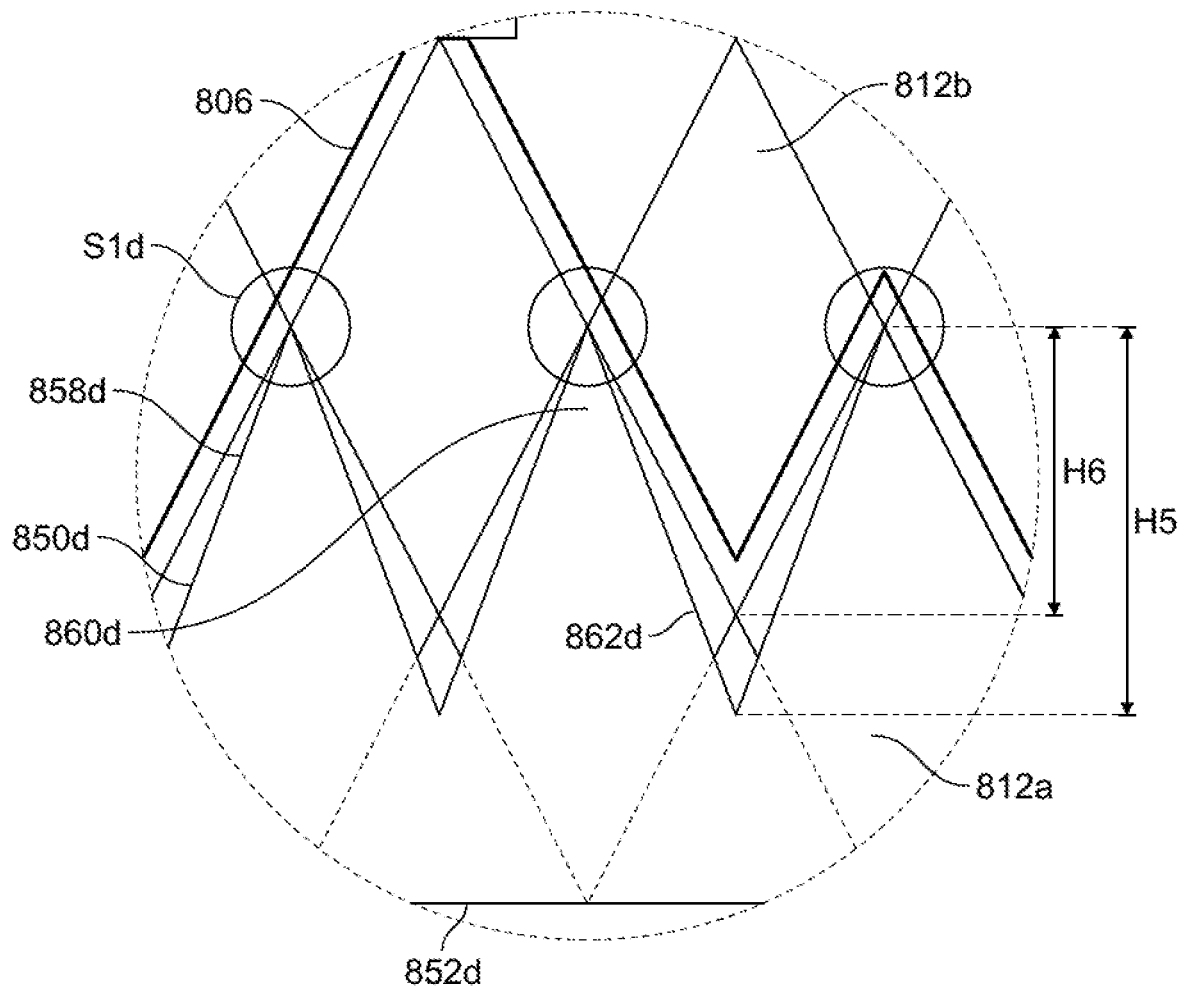

Referring to FIGS. 17D and 18D, the distal edge 858*d* of outer cuff 850*d* may be attached to stent 802 and/or to inner cuff 806 at locations that are spaced apart in the circumferential direction. Similar to outer cuffs 850*a*-*c*, the distal edge 858*d* of outer cuff 850*d* may, for example, be sutured to inner cuff 806 and/or to stent 802 at attachment points S1*d* located where each cell 812*b* in the second circumferential row of cells intersects with an adjacent cell in that same row. Distal edge 858*d* may include a plurality of repeating "V"-shapes similar to distal edge 858*c*. However, while distal edge 858*c* substantially follows the struts that are common to cells 812*a* and 812*b*, the troughs of the "V"-shapes of distal edge 858*d* may extend farther toward the inflow end of stent 802. In other words, distal edge 858*d* may include a plurality of peaks 860d that are substantially aligned with the points where adjacent cells 812b meet, and a plurality of troughs 862d that join each pair of adjacent peaks. However, troughs 862d may extend closer to the inflow edge of stent 802 than the troughs 862c of distal edge 858c, such that outer cuff 850d does not cover the points where adjacent cells 812a meet one another. In other words, the total height H5 that each peak 860d extends in the longitudinal direction of stent 802 is greater than the height H6 in the longitudinal direction of the stent between a proximal apex of cell 812b and a point of attachment S1d when the stent is in the expanded condition. The deeper troughs 862d of distal edge 858d compared to the troughs 862c of distal edge 858c may increase the likelihood that retrograde blood flow around the outside of the stent readily enters the space between the outer cuff and the inner cuff to help mitigate PV leak.

According to a first aspect of the disclosure, a prosthetic heart valve for replacing a native valve includes:

a stent having an inflow end, an outflow end, a plurality of cells formed by cell struts, a collapsed condition and an expanded condition;

a valve assembly disposed within the stent;

a first cuff annularly disposed adjacent the stent;

a second cuff having a proximal edge facing toward the inflow end of the stent and a distal edge facing toward the outflow end of the stent, the second cuff being annularly disposed about the stent radially outward of the first cuff and radially outward of the stent; and a plurality of fingers each having a first end coupled to a corresponding cell of the stent and a free end remote from the first end, the distal edge of the second cuff being coupled to the free ends of the fingers at spaced locations around a circumference of the stent, the free ends of the fingers being spaced radially outward of the corresponding cell in the expanded condition of the stent to position the distal edge of the second cuff radially outward of the corresponding cells of the stent at the spaced locations; and/or the cell struts may have a strut thickness in a radial direction of the stent, and the fingers may have a thickness in the radial direction of the stent that is less than the strut thickness; and/or the free ends of the fingers may be blunted; and/or the free ends of the fingers may include an eyelet; and/or the free ends of the fingers may include a cruciform structure; and/or each of the fingers may be formed of a single strut; and/or each of the fingers may include first and second struts each having a first end coupled to one of the plurality of cell struts and a second end, the second ends being coupled to one another; and/or the first and second struts of each finger may collectively form a "V" shape; and/or the distal edge of the second cuff may be coupled to an apex of the "V" shape; and/or each of the fingers may further include a third strut extending from an apex of the "V" shape, the distal edge of the second cuff being coupled to the third strut; and/or each of the cell struts may extend in an elongation direction, a first cell strut in each of the corresponding cells having a first width in a direction orthogonal to the elongation direction in first and second end portions of the first cell strut and a second width in the direction orthogonal to the elongation direction in a portion of the first cell strut intermediate the first and second end portions, the second width being less than the first width; and/or each of the cell struts forming the corresponding cells may have the first width in the direction orthogonal to the elongation direction in first and second end portions of the cell strut and the second width in the direction orthogonal to the elongation direction in a portion of the cell strut intermediate the first and second end portions; and/or the stent may include a plurality of commissure attachment features, an annulus section between the inflow end and the plurality of commissure attachment features, and an aortic section adjacent the outflow end, each of the cell struts in the annulus section extending in an elongation direction and having the first width in a direction orthogonal to the elongation direction in first and second end portions of the cell strut and the second width in the direction orthogonal to the elongation direction in a portion of the cell strut intermediate the first and second end portions; and/or the stent may include a plurality of commissure attachment features, an annulus section between the inflow end and the plurality of commissure attachment features, and an aortic section adjacent the outflow end, each of the cell struts extending in an elongation direction, each of the cell struts in the annulus section having a first width in a direction orthogonal to the elongation direction of the cell strut, and each of the cell struts in the aortic section having a second width in a direction orthogonal to the elongation direction of the cell strut, the second width being less than the first width; and/or each of the fingers in the expanded condition of the stent may curve toward the corresponding cell of the stent; and/or the plurality of cells may include a first annular row of cells extending around a circumference of the stent adjacent the inflow end, each of the corresponding cells being in the first annular row of cells; and/or the plurality of cells may include a first annular row of cells extending around a circumference of the stent adjacent the inflow end and a second annular row of cells extending around the circumference of the stent adjacent the first annular row of cells, each of the corresponding cells being in the second annular row of cells; and/or the stent may include a plurality of commissure attachment features, an annulus section between the inflow end and the plurality of commissure attachment features, and an aortic section adjacent the outflow end, each of the cell struts in the aortic section extending in an elongation direction, selected ones of the cell struts in the aortic section having a first width in a direction orthogonal to the elongation direction in first and second end portions of the selected cell strut and a second width in the direction orthogonal to the elongation direction in a portion of the selected cell strut intermediate the first and second end portions, the second width being less than the first width; and/or the plurality of cells may be arranged in annular rows of cells extending around a circumference of the stent, each of the selected ones of the cell struts being positioned in a single one of the annular rows; and/or the stent may include a plurality of commissure attachment features, an annulus section between the inflow end and the plurality of commissure attachment features, and an aortic section adjacent the outflow end, each of the cell struts in the annulus section extending in an elongation direction, a first group of the cell struts in the annulus section being connected to one of the commissure attachment features at an attachment point, each of the cell struts in the first group having a first width in a direction orthogonal to the elongation direction at a spaced distance from the attachment point and a second width in the direction orthogonal to the elongation direction at the attachment point, the second width being greater than the first width; and/or the stent may include a plurality of commissure attachment features, an annulus section between the inflow end and the plurality of commissure attachment features, and an aortic section adjacent the outflow end, each of the cell struts in the aortic section extending in an elongation direction, a first group of the cell struts in the aortic section being connected to one of the commissure attachment features at an attachment point, each of the cell struts in the first group having a first width in a direction orthogonal to the elongation direction at a spaced distance from the attachment point and a second width in the direction orthogonal to the elongation direction at the attachment point, the second width being greater than the first width.

According to another aspect of the disclosure, a prosthetic heart valve for replacing a native valve includes:

a stent having an inflow end, an outflow end, a plurality of cells formed by cell struts, a collapsed condition and an expanded condition;

a valve assembly disposed within the stent;

a first cuff annularly disposed adjacent the stent;

a second cuff having a proximal edge facing toward the inflow end of the stent and a distal edge facing toward the outflow end of the stent, the second cuff being annularly disposed about the stent and positioned radially outward of the first cuff and radially outward of the stent; and a third cuff having a proximal edge facing toward the inflow end of the stent and a distal edge facing toward the outflow end of the stent, the third cuff being annularly disposed about the stent and positioned radially outward of the second cuff, the distal edge of the second cuff being coupled to the stent at first attachment points spaced around a circumference of the stent, and the distal edge of the third cuff being coupled to the distal edge of the second cuff at second attachment points spaced around a circumference of the second cuff; and/or each of the second attachment points may be positioned circumferentially between an adjacent pair of the first attachment points; and/or the proximal edge of the second cuff and the proximal edge of the third cuff may be coupled to the inflow end of the stent substantially continuously along a circumference of the inflow end of the stent so that a first pocket is formed between the first cuff and the second cuff, and a second pocket is formed between the second cuff and the third cuff; and/or a single suture may couple the proximal edge of the second cuff and the proximal edge of the third cuff to the inflow end of the stent; and/or the second cuff may be adapted to billow outwardly of the first cuff upon retrograde blood flow into the first pocket, and the third cuff may be adapted to billow outwardly of the second cuff upon retrograde blood flow into the second pocket.

According to yet another aspect of the disclosure, a prosthetic heart valve for replacing a native valve includes:

a stent extending in an axial direction from an inflow end to an outflow end, the stent having a plurality of cells formed by cell strut, a collapsed condition and an expanded condition;

a valve assembly disposed within the stent;

a first cuff annularly disposed adjacent the stent; and a second cuff having a proximal edge facing toward the inflow end of the stent and a distal edge facing toward the outflow end of the stent, the second cuff being annularly disposed about the stent radially outward of the first cuff and radially outward of the stent, the second cuff including a pleat formed by at least two folds in the second cuff; and/or the folds of the pleat may be oriented in a circumferential direction of the stent; and/or the second cuff may include two or more separate pleats spaced apart from one another in the axial direction of the stent; and/or the folds of the pleat may be oriented in the axial direction of the stent; and/or the second cuff may include a plurality of groups of pleats, each one of the groups of pleats being spaced apart from other ones of the groups of pleats in a circumferential direction of the stent.

According to yet a further aspect of the disclosure a prosthetic heart valve for replacing a native valve includes:

a stent having an inflow end, an outflow end, a plurality of cells formed by cell struts, a collapsed condition and an expanded condition;

a valve assembly disposed within the stent;

a first cuff annularly disposed adjacent the stent; and a second cuff having a proximal edge facing toward the inflow end of the stent and a distal edge facing toward the outflow end of the stent, the second cuff being annularly disposed about the stent radially outward of the first cuff and radially outward of the stent, the distal edge including a plurality of peaks and a plurality of troughs, each trough connecting a pair of adjacent peaks, a distalmost portion of each peak being directly coupled to at least one of the first cuff and the stent; and/or the distalmost portion of each peak is coupled to at least one of the first cuff and the stent by a suture; and/or the plurality of peaks and the plurality of troughs each have a curved edge; and/or the plurality of peaks and the plurality of troughs each have a straight edge; and/or each peak includes a base at a proximalmost portion of the peak, the base having a first width in a circumferential direction of the stent, the distalmost portions of two adjacent peaks being spaced apart a second width in the circumferential direction of the stent, the second width being greater than the first width; and/or the base of each peak and the distalmost portion of each peak are spaced apart a first height in a longitudinal direction of the stent, the first height being equal to the second width; and/or a proximalmost portion of each peak has a first width in a circumferential direction of the stent, and proximalmost portions of two adjacent troughs are spaced apart a second width in the circumferential direction of the stent, the first width being smaller than the second width; and/or the first width is between one half and one fifth the second width; and/or each peak has a first height in a longitudinal direction of the stent, and each trough has a second height in the longitudinal direction of the stent, the first height being greater than the second height; and/or the plurality of cells include a first annular row of cells and a second annular row of cells, the first annular row of cells being positioned closer to the inflow end of the stent than is the second annular row of cells, each cell in the first annular row having a strut in common with a cell in the second annular row; and/or the distal edge of the second cuff is aligned with the struts in common when the stent is in the expanded condition; and/or each of the struts in common extends a first height in a longitudinal direction of the stent when the stent is in the expanded condition, and the distalmost portion of each peak is spaced apart from a proximalmost portion of each trough a second height in the longitudinal direction of the stent, the second height being greater than the first height.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, features of one embodiment described above may be combined with features of other embodiments described above.

The invention claimed is:

1. A prosthetic heart valve for replacing a native valve, comprising:
a stent having an inflow end, an outflow end, a plurality of cells formed by cell struts, a collapsed condition and an expanded condition;
a valve assembly disposed within the stent;
a first cuff annularly disposed adjacent the stent;
a second cuff having a proximal edge facing toward the inflow end of the stent and a distal edge facing toward the outflow end of the stent, the second cuff being annularly disposed about the stent radially outward of the first cuff and radially outward of the stent; and
a plurality of fingers each having a first end coupled to a corresponding cell of the stent and a free end remote from the first end, the free end extending into a space formed by the corresponding cell, the distal edge of the second cuff being coupled to the free ends of the fingers at spaced locations around a circumference of the stent, the free ends of the fingers being spaced radially outward of the corresponding cell in the expanded condition of the stent to position the distal edge of the second cuff radially outward of the corresponding cells of the stent at the spaced locations.

2. The prosthetic heart valve of claim 1, wherein the cell struts have a strut thickness in a radial direction of the stent, and the fingers have a thickness in the radial direction of the stent that is less than the strut thickness.

3. The prosthetic heart valve of claim 1, wherein the free ends of the fingers are blunted.

4. The prosthetic heart valve of claim 1, wherein the free ends of the fingers include an eyelet.

5. The prosthetic heart valve of claim 1, wherein the free ends of the fingers include a cruciform structure.

6. The prosthetic heart valve of claim 1, wherein each of the fingers is formed of a single strut.

7. The prosthetic heart valve of claim 1, wherein each of the fingers includes first and second struts each having a first end coupled to one of the plurality of cell struts and a second end, the second ends being coupled to one another.

8. The prosthetic heart valve of claim 7, wherein the first and second struts of each finger collectively form a "V" shape.

9. The prosthetic heart valve of claim 8, wherein the distal edge of the second cuff is coupled to an apex of the "V" shape.

10. The prosthetic heart valve of claim 8, wherein each of the fingers further includes a third strut extending from an apex of the "V" shape, the distal edge of the second cuff being coupled to the third strut.

11. The prosthetic heart valve of claim 1, wherein each of the cell struts extends in an elongation direction, a first cell strut in each of the corresponding cells having a first width in a direction orthogonal to the elongation direction in first and second end portions of the first cell strut and a second width in the direction orthogonal to the elongation direction in a portion of the first cell strut intermediate the first and second end portions, the second width being less than the first width.

12. The prosthetic heart valve of claim 11, wherein each of the cell struts forming the corresponding cells has the first width in the direction orthogonal to the elongation direction in first and second end portions of the cell strut and the second width in the direction orthogonal to the elongation direction in a portion of the cell strut intermediate the first and second end portions.

13. The prosthetic heart valve of claim 11, wherein the stent includes a plurality of commissure attachment features, an annulus section between the inflow end and the plurality of commissure attachment features, and an aortic section adjacent the outflow end, each of the cell struts in the annulus section having the first width in the direction orthogonal to the elongation direction in first and second end portions of the cell strut and the second width in the direction orthogonal to the elongation direction in a portion of the cell strut intermediate the first and second end portions.

14. The prosthetic heart valve of claim 1, wherein the stent includes a plurality of commissure attachment features, an annulus section between the inflow end and the plurality of commissure attachment features, and an aortic section adjacent the outflow end, each of the cell struts extending in an elongation direction, each of the cell struts in the annulus section having a first width in a direction orthogonal to the elongation direction of the cell strut, and each of the cell struts in the aortic section having a second width in the direction orthogonal to the elongation direction of the cell strut, the second width being less than the first width.

15. The prosthetic heart valve of claim 1, wherein each of the fingers in the expanded condition of the stent curves toward the corresponding cell of the stent.

16. The prosthetic heart valve of claim 1, wherein the plurality of cells includes a first annular row of cells extending around a circumference of the stent adjacent the inflow end, each of the corresponding cells being in the first annular row of cells.

17. The prosthetic heart valve of claim 1, wherein the plurality of cells includes a first annular row of cells extending around a circumference of the stent adjacent the inflow end and a second annular row of cells extending around the circumference of the stent adjacent the first annular row of cells, each of the corresponding cells being in the second annular row of cells.

18. The prosthetic heart valve of claim 1, wherein the stent includes a plurality of commissure attachment features, an annulus section between the inflow end and the plurality of commissure attachment features, and an aortic section adjacent the outflow end, each of the cell struts in the aortic section extending in an elongation direction, selected ones of the cell struts in the aortic section having a first width in a direction orthogonal to the elongation direction in first and second end portions of the selected cell strut and a second width in the direction orthogonal to the elongation direction in a portion of the selected cell strut intermediate the first and second end portions, the second width being less than the first width.

19. The prosthetic heart valve of claim 18, wherein the plurality of cells are arranged in annular rows of cells extending around a circumference of the stent, each of the selected ones of the cell struts being positioned in a single one of the annular rows.

20. The prosthetic heart valve of claim 1, wherein the stent includes a plurality of commissure attachment features, an annulus section between the inflow end and the plurality of commissure attachment features, and an aortic section adjacent the outflow end, each of the cell struts in the annulus section extending in an elongation direction, a first group of the cell struts in the annulus section being connected to one of the commissure attachment features at an attachment point, each of the cell struts in the first group having a first width in a direction orthogonal to the elongation direction at a spaced distance from the attachment point and a second width in the direction orthogonal to the elongation direction at the attachment point, the second width being greater than the first width.

21. The prosthetic heart valve of claim 1, wherein the stent includes a plurality of commissure attachment features, an annulus section between the inflow end and the plurality of commissure attachment features, and an aortic section adjacent the outflow end, each of the cell struts in the aortic section extending in an elongation direction, a first group of the cell struts in the aortic section being connected to one of the commissure attachment features at an attachment point, each of the cell struts in the first group having a first width in a direction orthogonal to the elongation direction at a spaced distance from the attachment point and a second width in the direction orthogonal to the elongation direction at the attachment point, the second width being greater than the first width.

* * * * *